United States Patent
Ding et al.

(10) Patent No.: US 11,426,230 B2
(45) Date of Patent: Aug. 30, 2022

(54) SURGICAL INSTRUMENTS CAPABLE OF BEING SELECTIVELY DISASSEMBLED TO FACILITATE REPLACEMENT OF DISPOSABLE COMPONENTS AND/OR STERILIZATION OF REUSABLE COMPONENTS

(71) Applicant: COVIDIEN LP, Mansfield, MA (US)

(72) Inventors: Weijiang Ding, Shanghai (CN); Yuanxun Li, Shanghai (CN); Sarfraz Ahamed Syed, Karnataka (IN); Mimi Ding, Shanghai (CN); Mingfeng Xu, Hefei (CN); Pu Liu, Shanghai (CN); Kai Liu, Hunan (CN); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 922 days.

(21) Appl. No.: 15/418,877

(22) PCT Filed: Jul. 30, 2014

(86) PCT No.: PCT/CN2014/083267
§ 371 (c)(1),
(2) Date: Jan. 30, 2017

(87) PCT Pub. No.: WO2016/015233
PCT Pub. Date: Feb. 4, 2016

(65) Prior Publication Data
US 2017/0181789 A1    Jun. 29, 2017

(51) Int. Cl.
*A61B 18/14*      (2006.01)
*A61B 17/295*      (2006.01)
(Continued)

(52) U.S. Cl.
CPC ........ *A61B 18/1445* (2013.01); *A61B 17/295* (2013.01); *A61B 34/30* (2016.02);
(Continued)

(58) Field of Classification Search
CPC .............. A61B 17/295; A61B 18/1445; A61B 2017/0046; A61B 2017/2929;
(Continued)

(56) References Cited

U.S. PATENT DOCUMENTS

| 2,113,246 A | 4/1938 | Wappler |
| 4,084,594 A | 4/1978 | Mosior |

(Continued)

FOREIGN PATENT DOCUMENTS

CN          103584912 A      2/2014

OTHER PUBLICATIONS

Notification of the First Office Action issued in corresponding CN application No. 201480080984.7 dated Dec. 25, 2018, with English translation, 14 pages.

*Primary Examiner* — Thomas A Giuliani
*Assistant Examiner* — Christine A Dedoulis
(74) *Attorney, Agent, or Firm* — Carter, DeLuca & Farrell LLP

(57) ABSTRACT

A forceps includes a first portion and a second portion. The first portion includes a shaft, an end effector assembly disposed at a distal end of the shaft, and a drive assembly including a drive bar. The end effector assembly includes jaw members movable between spaced-apart and approximated positions. The drive bar is slidably disposed within the shaft and coupled to the end effector assembly such that translation of the drive bar relative to the shaft moves the jaw members between the spaced-apart and approximated positions. The second portion includes a housing (or portion thereof) and a handle assembly including a movable handle (Continued)

that is coupled to the housing and movable relative thereto between first and second positions. The first and second portions are releasably couplable with one another to operably couple the movable handle with the drive bar such that moving the movable handle actuates the jaw members.

8 Claims, 11 Drawing Sheets

(51) Int. Cl.
    *A61B 17/29* (2006.01)
    *A61B 17/00* (2006.01)
    *A61B 90/00* (2016.01)
    *A61B 34/30* (2016.01)
    *A61B 18/00* (2006.01)

(52) U.S. Cl.
    CPC ........... *A61B 2017/0046* (2013.01); *A61B 2017/2929* (2013.01); *A61B 2018/00601* (2013.01); *A61B 2018/1455* (2013.01); *A61B 2090/0813* (2016.02)

(58) Field of Classification Search
    CPC .. A61B 2018/00601; A61B 2018/1455; A61B 34/30; A61B 2090/0813; A61B 2018/00178
    See application file for complete search history.

(56) References Cited

U.S. PATENT DOCUMENTS

| | | | |
|---|---|---|---|
| 5,035,248 A | 7/1991 | Zinnecker | |
| 5,308,358 A | 5/1994 | Bond et al. | |
| 5,318,040 A | 6/1994 | Kensey et al. | |
| 5,486,185 A | 1/1996 | Freitas et al. | |
| 5,507,774 A | 4/1996 | Holmes et al. | |
| 5,571,100 A | 11/1996 | Goble et al. | |
| 5,603,723 A | 2/1997 | Aranyi et al. | |
| 5,810,876 A | 9/1998 | Kelleher | |
| 5,830,231 A | 11/1998 | Geiges, Jr. | |
| 5,913,857 A | 6/1999 | Ritchart et al. | |
| 5,913,874 A | 6/1999 | Berns et al. | |
| 5,984,939 A | 11/1999 | Yoon | |
| 6,077,290 A | 6/2000 | Marini | |
| 6,514,247 B1 * | 2/2003 | McGaffigan | A61B 18/1477 606/41 |
| 7,025,775 B2 | 4/2006 | Gadberry et al. | |
| 7,632,270 B2 | 12/2009 | Livneh | |
| 8,012,154 B2 | 9/2011 | Livneh | |
| 8,100,907 B2 | 1/2012 | Aue | |
| 8,246,608 B2 * | 8/2012 | Omori | A61B 34/70 606/1 |
| 8,361,072 B2 | 1/2013 | Dumbauld et al. | |
| 9,011,471 B2 * | 4/2015 | Timm | A61B 18/1445 606/169 |
| 2006/0129186 A1 | 6/2006 | Gadberry et al. | |
| 2008/0004656 A1 | 1/2008 | Livneh | |
| 2008/0039892 A1 | 2/2008 | Mitsuishi et al. | |
| 2010/0145334 A1 * | 6/2010 | Olson | A61B 18/1445 606/48 |
| 2010/0312242 A1 | 12/2010 | Odom | |
| 2011/0077649 A1 * | 3/2011 | Kingsley | A61B 18/1445 606/52 |
| 2011/0288452 A1 * | 11/2011 | Houser | A61L 2/07 601/2 |
| 2012/0116264 A1 * | 5/2012 | Haberstich | A61B 34/25 601/2 |
| 2012/0191091 A1 * | 7/2012 | Allen | A61B 18/1206 606/52 |
| 2012/0316601 A1 * | 12/2012 | Twomey | A61B 17/2909 606/205 |
| 2013/0190755 A1 * | 7/2013 | Deborski | A61B 18/14 606/41 |
| 2013/0304059 A1 | 11/2013 | Allen, IV et al. | |
| 2014/0276736 A1 * | 9/2014 | Worrell | A61B 18/1445 606/33 |

\* cited by examiner

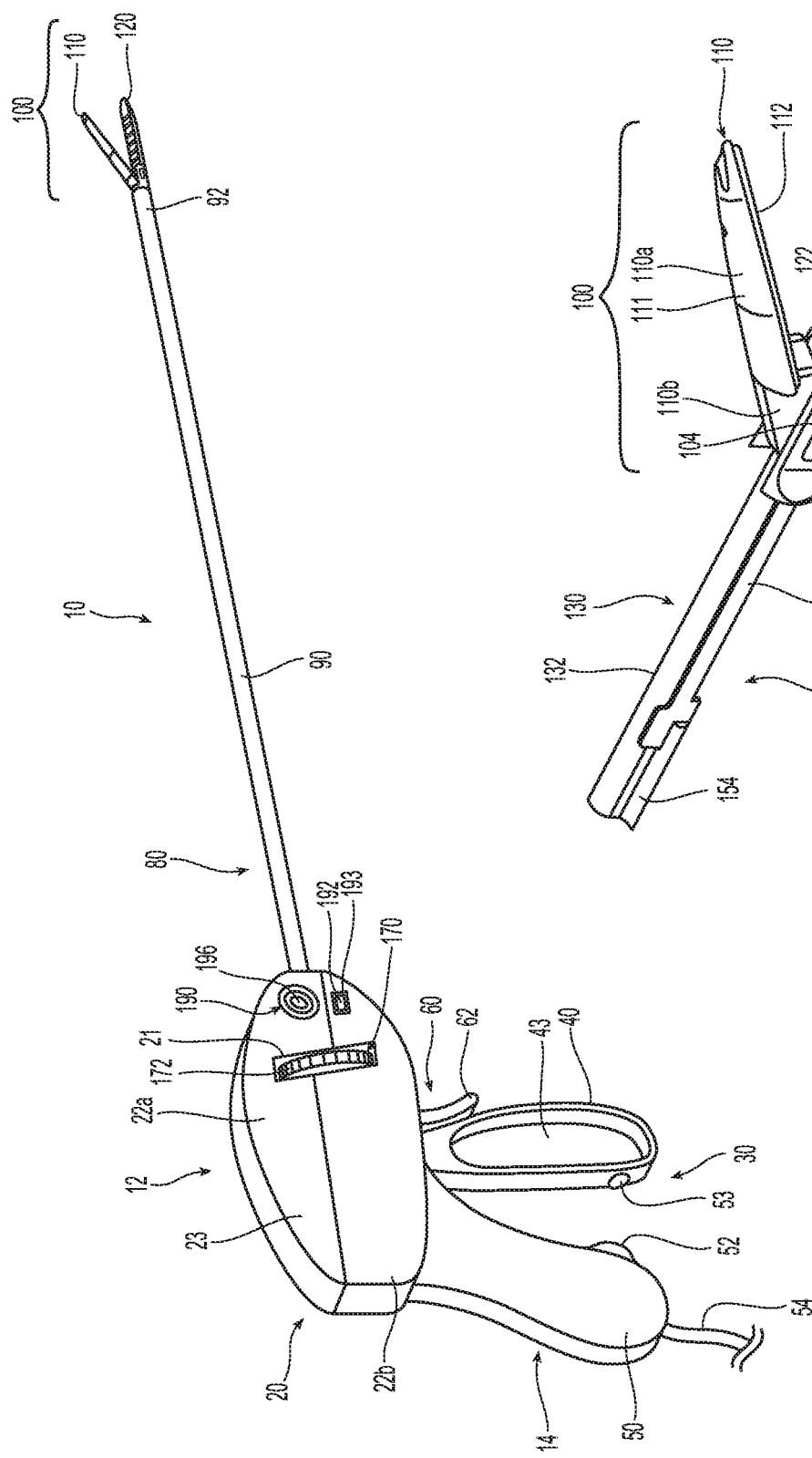
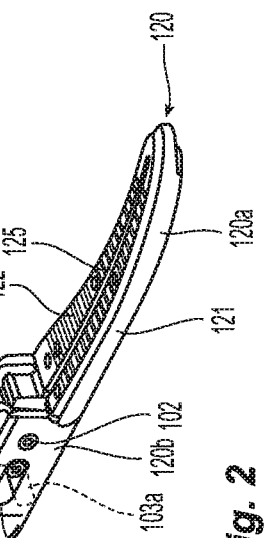
Fig. 1
Fig. 2

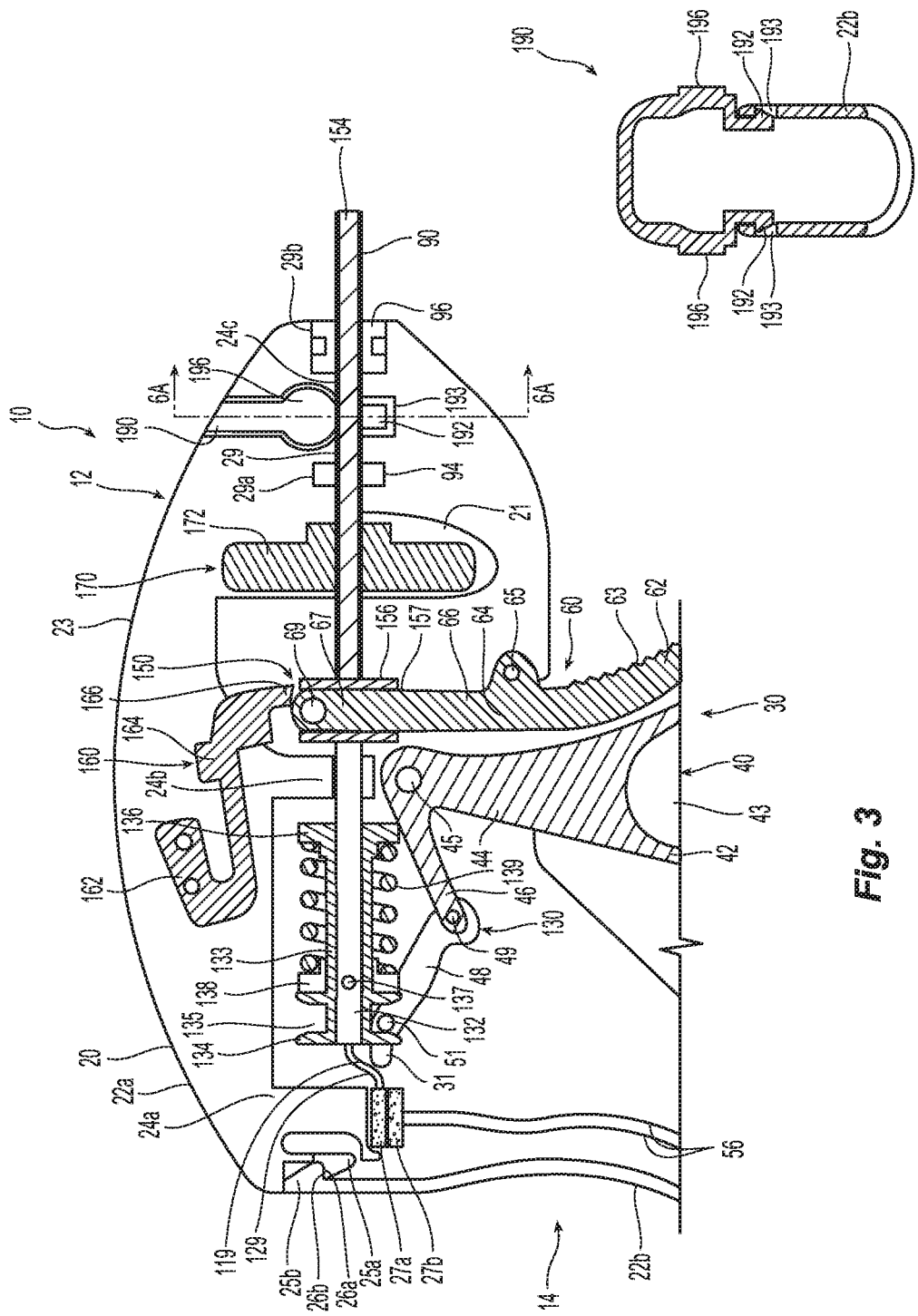

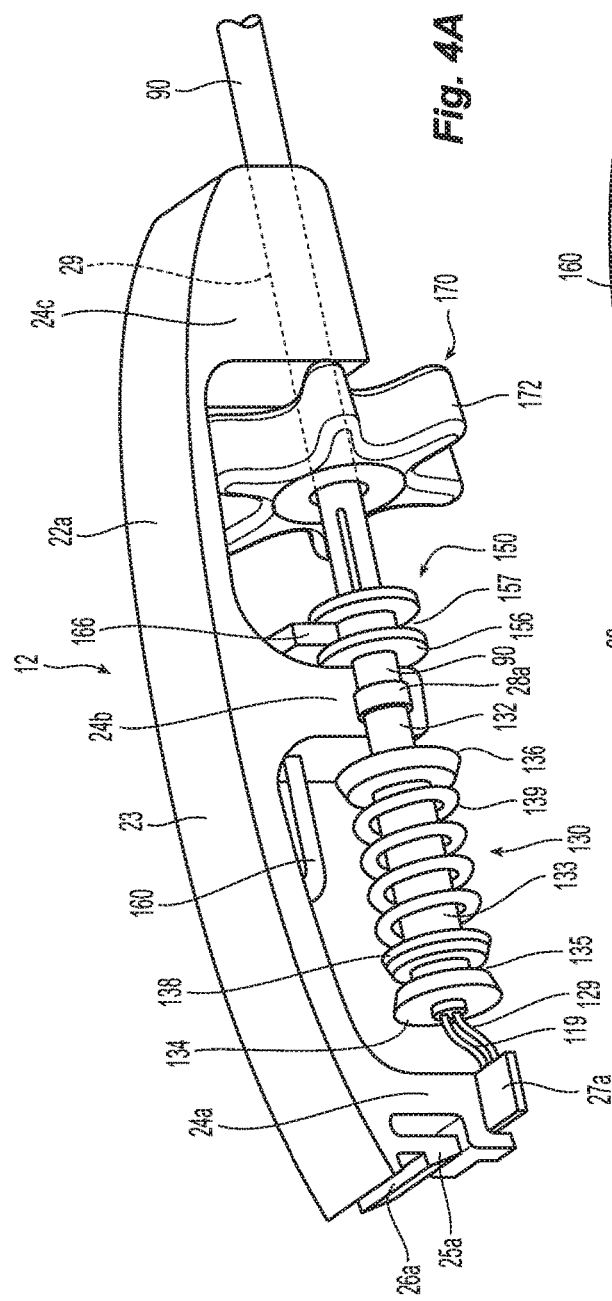
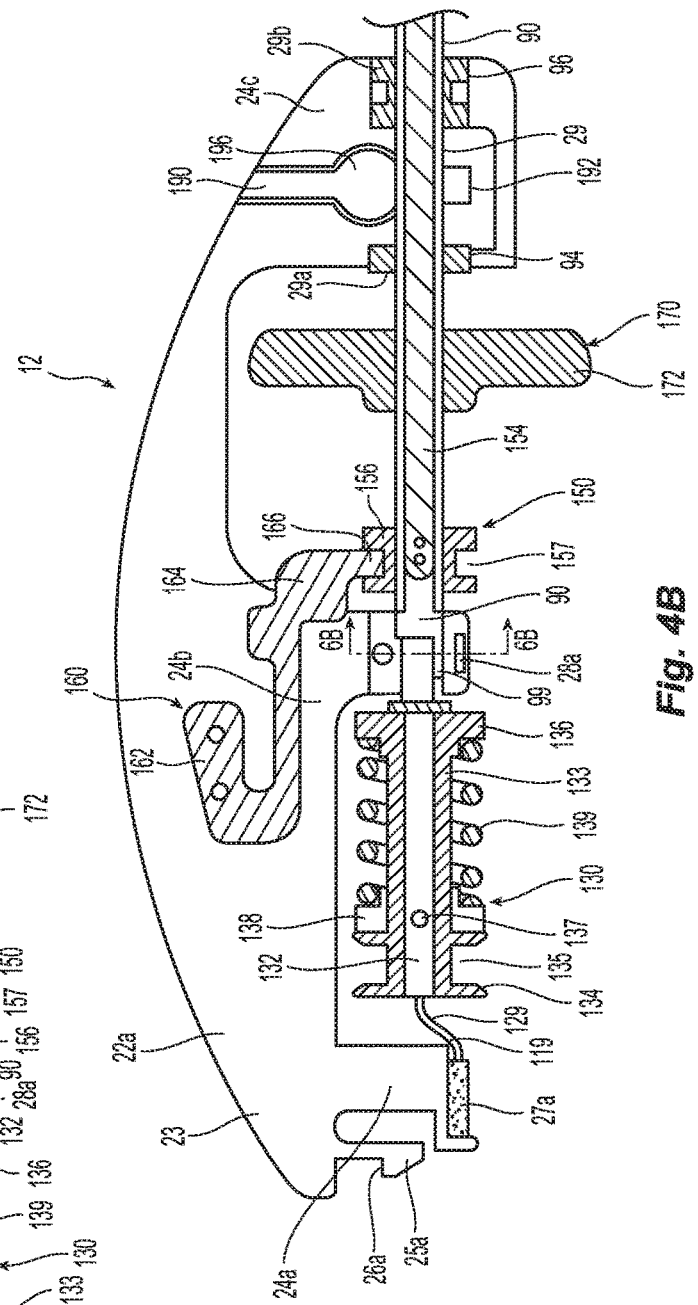
Fig. 4A
Fig. 4B

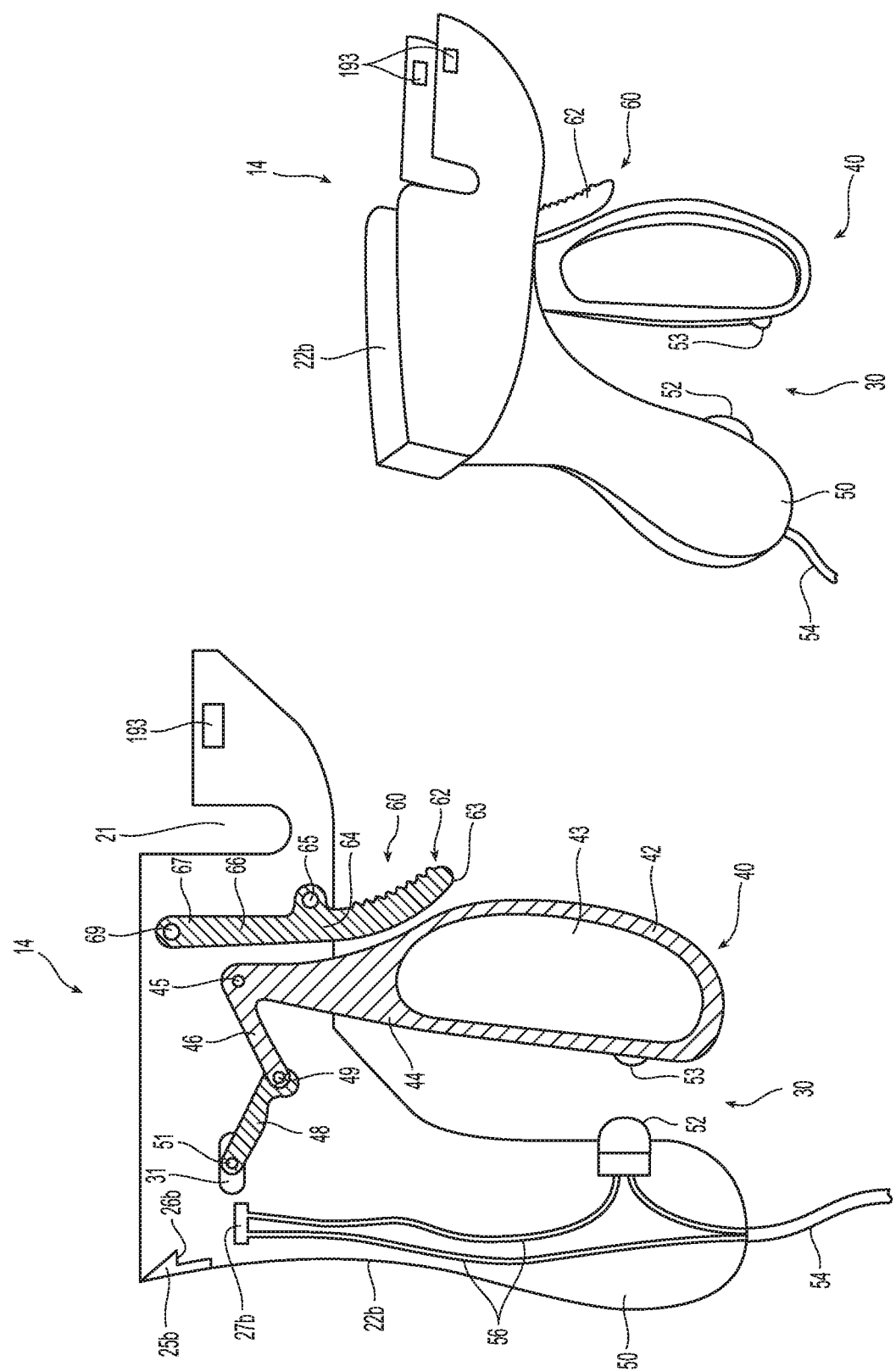

SURGICAL INSTRUMENTS CAPABLE OF BEING SELECTIVELY DISASSEMBLED TO FACILITATE REPLACEMENT OF DISPOSABLE COMPONENTS AND/OR STERILIZATION OF REUSABLE COMPONENTS

CROSS REFERENCE TO RELATED APPLICATION

The present application is a U.S. National Stage Application under 35 U.S.C. §371(a) of PCT/CN2014/083267 filed Jul. 30, 2014, the entire contents of which are incorporated by reference herein.

BACKGROUND

Technical Field

The present disclosure relates generally to surgical instruments and, more particularly, to surgical instruments capable of being selectively disassembled to facilitate replacement of any disposable component of the surgical instrument and/or sterilization of any reusable component of the surgical instrument for reuse.

Background of Related Art

Generally, surgical instruments are classified as disposable, e.g., instruments that are discarded after a single use; partially-reusable or reposable, e.g., instruments including both disposable components that are discarded after a single use and reusable components that are sterilizable for repeated use; or reusable, e.g., instruments that are fully sterilizable for repeated use. As can be appreciated, reusable and partially-reusable surgical instruments help reduce the costs associated with the particular surgical procedures for which they are used. However, although reusable and partially-reusable surgical instruments are cost-effective, the requirements of these reusable and partially-reusable surgical instruments present significant design challenges. More specifically, reusable and partially-reusable surgical instruments must be capable of performing the same functions as their disposable counterparts, resist significant degradation during their useful lives, allow for adequate sterilization of any reusable components, and allow for efficient replacement of any disposable components.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a forceps is provided including a first portion and a second portion. The first portion of the forceps includes a shaft, an end effector assembly, and a drive assembly. The end effector assembly is disposed at a distal end of the shaft and includes first and second jaw members movable relative to one another between a spaced-apart position and an approximated position. The drive assembly includes a drive bar slidably disposed within the shaft and coupled to the end effector assembly at a distal end of the drive bar such that translation of the drive bar relative to the shaft moves the first and second jaw members between the spaced-apart and approximated positions. The second portion of the forceps includes the entirety of or a portion of a housing, and a handle assembly including a movable handle coupled to the housing. The movable handle is movable relative to the housing between a first position and a second position. The first and second portions of the forceps are releasably couplable with one another. Coupling of the first and second portions with one another operably couples the movable handle with the drive bar such that moving the movable handle between the first and second positions moves the jaw members between the spaced-apart and approximated positions.

In an aspect of the present disclosure, the drive assembly includes a mandrel that is coupled to the drive bar and defines a slot, and the handle assembly includes one or more transverse pins coupled to the movable handle. Upon coupling of the first and second portions with one another, the transverse pin(s) is received within the slot of the mandrel such that moving the movable handle between the first and second positions moves the jaw members between the spaced-apart and approximated positions.

In another aspect of the present disclosure, the drive assembly includes a mandrel that is coupled to the drive bar and defines a slot, and the movable handle includes one or more tracks disposed thereon. Upon coupling of the first and second portions with one another, the track(s) is received within the slot of the mandrel such that moving the movable handle between the first and second positions moves the jaw members between the spaced-apart and approximated positions.

In still another aspect of the present disclosure, the first portion includes a first housing component supporting the shaft and the drive assembly, and the second portion includes a second housing component having the handle assembly coupled thereto. Upon coupling of the first and second portions with one another, the first and second housing components are engaged with one another to fully form the housing.

In yet another aspect of the present disclosure, the second portion includes the entire housing. The housing includes a body and a cover that is movable relative to the body from a closed position, wherein the body and the cover cooperate to enclose an interior of the housing, and an open position, wherein the interior of the housing is exposed to permit insertion of the first portion at least partially into the housing.

In still yet another aspect of the present disclosure, the first portion of the forceps includes a first electrical connector electrically coupled to one or both of the first and second jaw members and the second portion of the forceps includes a second electrical connector adapted to connect to a source of energy. Upon coupling of the first and second portions with one another, the first and second electrical connectors are electrically coupled with one another to enable energy to be supplied from the energy source to one or both of the jaw members. The electrical connectors may be contact plates configured to mate with one another upon coupling of the first and second portions with one another, although other suitable electrical connector components are also contemplated.

In another aspect of the present disclosure, the first portion includes a knife assembly. The knife assembly has a knife drive bar slidably disposed within the shaft and a knife extending distally from the knife drive bar. The knife assembly is configured such that translation of the knife drive bar relative to the shaft moves the knife relative to the end effector assembly between a retracted position and an extended position. In the extended position, the knife extends between the first and second jaw members, e.g., to cut tissue grasped therebetween. In such aspects, the second portion includes a trigger assembly including a trigger. The trigger is coupled to the housing and is movable relative thereto between an un-actuated position and an actuated position. As a result of this configuration, coupling of the first and second portions with one another operably couples the trigger with the knife drive bar such that moving the trigger between the un-actuated and actuated positions moves the knife between the retracted and extended positions.

In aspects of the present disclosure, the knife assembly includes a mandrel coupled to the knife drive bar and defining a slot. In such aspects, the trigger includes one or more protrusions disposed thereon. Upon coupling of the first and second portions with one another, the protrusion(s) is received within the slot of the mandrel such that moving the trigger between the un-actuated and actuated positions moves the knife between the retracted and extended positions. Alternatively, the knife assembly may include a collar coupled to the knife drive bar and including a transverse pin engaged thereto, while the trigger defines one or more slots. In such aspects, upon coupling of the first and second portions with one another, the transverse pin is received within the at least one slot of the trigger such that moving the trigger between the un-actuated and actuated positions moves the knife between the retracted and extended positions.

In another aspect of the present disclosure, the first portion includes a knife lockout member movable between a locked position, wherein the knife lockout member is coupled to the knife drive bar to inhibit translation of the knife drive bar relative to the shaft, and an unlocked position, wherein the knife lockout member is decoupled from the knife drive bar to permit translation of the knife drive bar relative to the shaft. The knife lockout member is configured to move from the locked position to the unlocked position upon coupling of the first and second portions with one another, and to return to the locked position upon decoupling of the first and second portions from one another.

In still yet another aspect of the present disclosure, the first portion includes a rotation assembly having a rotation wheel coupled to the shaft and the drive assembly. In such aspects, when the first and second portions are coupled with one another, the rotation wheel is rotatable relative to the second portion to rotate the end effector assembly relative to the second portion.

Another forceps provided in accordance with aspects of the present disclosure includes first and second portions. The first portion has a first housing component, a shaft rotatable supported by the first housing component, an end effector assembly, and a drive assembly. The end effector assembly is disposed at a distal end of the shaft and includes first and second jaw members movable relative to one another between a spaced-apart position and an approximated position. The drive assembly includes a drive bar slidably disposed within the shaft and coupled to the end effector assembly at a distal end of the drive bar such that translation of the drive bar relative to the shaft moves the first and second jaw members between the spaced-apart and approximated positions. The second portion of the forceps includes a second housing component and a handle assembly. The handle assembly includes a movable handle coupled to the second housing component and movable relative thereto between a first position and a second position. The first and second portions of the forceps are releasably couplable with one another. Upon such coupling, the movable handle is operably coupled with the drive bar such that moving the movable handle between the first and second positions moves the jaw members between the spaced-apart and approximated positions, and the first and second housing components are engaged with one another to form a housing that at least partially encloses the drive assembly and the handle assembly therein.

In an aspect of the present disclosure, the first and second housing components include corresponding engagement features for releasably engaging the first and second housing components with one another.

In another aspect of the present disclosure, the first portion includes a knife assembly having a knife drive bar slidably disposed within the shaft and a knife extending distally from the knife drive bar. The knife assembly is configured such that translation of the knife drive bar relative to the shaft moves the knife relative to the end effector assembly between a retracted position and an extended position. The knife extends between the first and second jaw members in the extended position. In such aspects, the second portion includes a trigger assembly including a trigger coupled to the second housing component and movable relative thereto between an un-actuated position and an actuated position. Coupling of the first and second portions with one another according to these aspects operably couples the trigger with the knife drive bar such that moving the trigger between the un-actuated and actuated positions moves the knife between the retracted and extended positions.

In still yet another aspect of the present disclosure, the first housing component includes a first electrical contact plate coupled thereto that is electrically coupled to either or both of the first and second jaw members. In such aspects, the second housing component includes a second electrical contact plate coupled thereto that is adapted to connect to a source of energy. Coupling of the first and second portions with one another according to such aspects electrically couples the first and second electrical contact plates with one another to enable energy to be supplied from the energy source to the first and/or second jaw members.

Yet another forceps provide in accordance with aspects of the present disclosure includes a first portion and a second portion. The first portion includes a shaft an end effector assembly disposed at a distal end of the shaft, and a drive assembly. The end effector assembly has first and second jaw members movable relative to one another between a spaced-apart position and an approximated position. The drive assembly includes a drive bar slidably disposed within the shaft and coupled to the end effector assembly at a distal end of the drive bar such that translation of the drive bar relative to the shaft moves the first and second jaw members between the spaced-apart and approximated positions. The second portion of the forceps includes a housing and a handle assembly having a movable handle coupled to the housing and movable relative thereto between a first position and a second position. The first portion of the forceps is insertable into the housing of the second portion of the forceps for releasable coupling therewith. Coupling of these first and second portions in this manner operably couples the movable handle with the drive bar such that moving the movable handle between the first and second positions moves the jaw members between the spaced-apart and approximated positions.

In an aspect of the present disclosure, the housing includes a body and a cover movable relative to the body from a closed position, wherein the body and the cover cooperate to enclose an interior of the housing, and an open position, wherein the interior of the housing is exposed to permit insertion of the first portion at least partially into the body.

In another aspect of the present disclosure, the first portion includes a knife assembly having a knife drive bar slidably disposed within the shaft and a knife extending distally from the knife drive bar. The knife assembly is configured such that translation of the knife drive bar relative to the shaft moves the knife relative to the end effector assembly between a retracted position and an extended position. The knife extends between the first and second jaw members in the extended position. In such aspects, the second portion includes a trigger assembly including a trigger coupled to the housing and movable relative thereto between an un-actuated position and an actuated position. Coupling of the first and second portions with one another operably couples the trigger with the knife drive bar such that moving the trigger between the un-actuated and actuated positions moves the knife between the retracted and extended positions.

In still another aspect of the present disclosure, the first portion of the forceps includes a rotation assembly having a rotation wheel coupled to the shaft and the drive assembly, and the housing of the second portion of the forceps defines one or more slots. When the first portion is inserted into the housing of the second portion, the rotation wheel extends at least partially through the slot(s) to permit rotation of the rotation wheel from an exterior of the housing. Rotation of the rotation wheel effects rotation of the end effector assembly relative to the second portion of the forceps.

A system provided in accordance with aspects of the present disclosure includes a forceps, e.g., a forceps according to any of the aspects detailed above. The system further includes a tool having one or more support members. The support member(s) is configured to releasably engage the first portion of the forceps to facilitate releasable coupling of the first and second portions of the forceps with one another.

In an aspect of the present disclosure, the tool of the system further includes an actuation assembly having an actuator and a foot coupled to the actuator. The actuator is selectively movable from an initial position to an actuated position for urging the foot into contact with the first portion of the forceps to disengage the support member(s) from the first portion of the forceps.

In another aspect, the support member(s) includes a pair of fingers interconnected by a living hinge and defining a recess therebetween. The support member(s) is configured to receive the first portion within the recess to releasably engage the first portion therewith.

In yet another aspect of the present disclosure, the tool further includes a handle configured to facilitate grasping and manipulating the tool.

BRIEF DESCRIPTION OF THE DRAWINGS

Various aspects and features of the present disclosure are described hereinbelow with reference to the drawings wherein like reference numerals identify similar or identical elements:

FIG. 1 is a perspective view of an endoscopic surgical forceps provided in accordance with the present disclosure:

FIG. 2 is a perspective view of the distal end of the forceps of FIG. 1 with the shaft removed to show the internal components therein;

FIG. 3 is a partial, longitudinal, cross-sectional view of the forceps of FIG. 1 with the movable handle disposed in an initial position;

FIG. 4A is a perspective, cut-away view of the proximal end of the first portion of the forceps of FIG. 1;

FIG. 4B is a longitudinal, cross-sectional view of the proximal end of the first portion of the forceps of FIG. 1;

FIG. 5A is a perspective view of the second portion of the forceps of FIG. 1;

FIG. 5B is a longitudinal, cross-sectional view of the second portion of the forceps of FIG. 1;

FIG. 6A is a transverse, cross-sectional view taken along section line 6A-6A in FIG. 3;

DETAILED DESCRIPTION

Figure 6B:
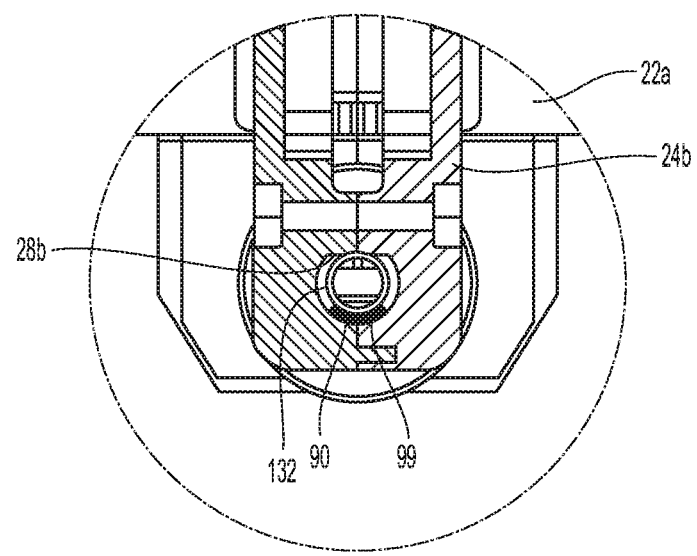
FIG. 6B is a transverse, cross-sectional view taken along section line 6B-6B in FIG. 4B.

Turning to FIGS. 1-6B, an endoscopic surgical forceps provided in accordance with the present disclosure is shown generally identified by reference numeral 10. As described in greater detail below, forceps 10 is configured for selective disassembly to facilitate replacement of any disposable component of forceps 10 and/or sterilization of any reusable component of forceps 10. The selective disassembly of forceps 10 also enables customization in that it allows an user to select a particular component or components for use in accordance with a particular surgical procedure to be performed, a patient's anatomy or condition, a surgeon's preference, and/or other factors. Although detailed herein with respect to forceps 10, the aspects and features of the present disclosure are equally applicable for use with any suitable surgical instrument incorporating disposable, reusable, and/or replaceable components.

Forceps 10 is formed from a first portion 12 (FIGS. 4A and 4B) and a second portion 14 (FIGS. 5A and 5B) and includes a housing 20 having first and second housing components 22a, 22b, a handle assembly 30, a trigger assembly 60, and a transmission assembly 80 which includes a shaft 90, an end effector assembly 100, a drive assembly 130, a knife assembly 150, and a rotating assembly 170. First portion 12 of forceps 10 includes first housing component 22a of housing 20 and transmission assembly 80, which is coupled to and supported by first housing component 22a. Second portion 14 of forceps 10 includes second housing component 22b of housing 20 and handle assembly 30 and trigger assembly 60, which are coupled to and supported by second housing component 22b. First and second portions 12, 14, respectively, of forceps 10 are releasably engagable with one another to concurrently or near-concurrently mechanically and electrically couple the various cooperating components of first and second portions 12, 14 with one another, obviating the need to separately couple the various cooperating components of first and second portions 12, 14 to one another. More specifically, and as will be described in greater detail below, engagement of first and second portions 12, 14 of forceps 10 with one another engages first and second housing components 22a, 22b with one another to form housing 20, operably couples handle assembly 30 and trigger assembly 60 with drive assembly 130 and knife assembly 150, respectively, and electrically couples end effector assembly 100 to a source of energy, e.g., a generator (not shown), and activation button 52. On the other hand, as also will be described in greater detail below, disengagement of first and second portions 12, 14, respectively, from one another disengages first and second housing components 22a, 22b from one another, decouples transmission assembly 80 from handle assembly 30 and trigger assembly 60, and electrically disconnects end effector assembly 100 from the source of energy (not shown) and activation button 52.

In one particular configuration, first portion 12 of forceps 10 is configured as a disposable portion, while second portion 14 of forceps 10 is configured as a sterilizable, reusable portion. Thus, after each use: first and second portions 12, 14 are disengaged from one another; first portion 12 is discarded; second portion 14 is sterilized and/or otherwise prepared for reuse; and an un-used first portion 12 is engaged to the sterilized second portion 14. However, other configurations are also contemplated. That is, either or both of first and second portions 12, 14, or any of the components thereof, may be configured as disposable or reusable portions or components.

Referring to FIGS. 1-4B, first portion 12 of forceps 10, as mentioned above, includes first housing component 22a of housing 20 and transmission assembly 80, which is coupled to and supported by first housing component 22a. First housing component 22a includes a body 23 and a plurality of supports extending from body 23, e.g., a proximal support 24a, an intermediate support 24b, and a distal support 24c (see FIG. 3). Proximal support 24a includes a resilient engagement finger 25a defining a shoulder 26a at the free end thereof that is configured for mating engagement with a corresponding shoulder 26b of an engagement member 25b of second housing component 22b (see FIG. 5B) to releasably engage first and second housing components 22a, 22b to one another at the proximal ends thereof. Proximal support 24a also retains a first contact plate 27a. First and second lead wires 119, 129 extend from first contact plate 27a, through drive bar 132 and/or shaft 90, ultimately connecting to plates 112, 122 of first and second jaw members 110, 120, respectively. First contact plate 27a is configured to electrically couple with second contact plate 27b of second housing component 22b (FIG. 5B) to electrically couple lead wires 119, 129 and, thus, plates 112, 122 of jaw members 110, 120 of end effector assembly 100 with activation button 52 and the source of energy.

Intermediate support 24b of first housing component 22a includes a band 28a (FIG. 4A) disposed about shaft 90 to support the proximal end of shaft 90 within first housing component 22a while also permitting rotation of shaft 90 relative to first housing component 22a. More specifically and with momentary reference to FIG. 6B, shaft 90 includes a tongue 99 at the proximal end thereof that extends through and is supported by intermediate support 24b. Band 28a and intermediate support 24b cooperate to define a generally annular opening for receiving tongue 99 of shaft 90, except that an upper portion of the opening is cut-off to define a shelf 28b. As a result of this configuration and, more particularly, the interaction of tongue 99 and shelf 28b, shaft 90 is only permitted to be rotated relative to first housing component 22a by about 180 degrees in either direction, although other configurations are also contemplated.

Referring again to FIGS. 1-4B, distal support 24c defines a lumen 29 having an enlarged proximal portion 29a and an enlarged distal portion 29b. Shaft 90 is slidably received within lumen 29 and includes a proximal ferrule 94 mounted thereon that is received within enlarged proximal portion 29a of lumen 29 and a distal ferrule 96 mounted thereon that is received within enlarged distal portion 29b of lumen 29. As such, shaft 90 is maintained in fixed longitudinal position relative to first housing component 22a while still being permitted to rotate relative to first housing component 22a. Similar to proximal support 24a, distal support 24c also includes engagement features for releasably engaging first and second housing components 22a, 22b to one another at the distal ends thereof. More specifically, with additional reference to FIG. 6A, a resilient U-shaped locking member 190 is disposed about distal support 24c and includes engagement protrusions 192 defined at the free ends of U-shaped locking member 190. Protrusions 192 are configured for engagement within corresponding apertures 193 defined within second housing component 22b to releasably engage first and second housing components 22a, 22b with one another at their proximal ends. U-shaped locking member 190 biases protrusions 192 outwardly to facilitate engagement within apertures 193 upon positioning adjacent thereto. Release buttons 196 are positioned adjacent protrusions 192 and protrude from first housing component 22a on either side thereof. Release buttons 196 are selectively squeezable to urge protrusions 192 inwardly against the bias to disengage protrusions 192 from apertures 193, thereby disengaging first and second housing components 22a, 22b from one another at the distal ends thereof.

Referring again to FIGS. 1-4B, as mentioned above, transmission assembly 80 includes shaft 90, end effector assembly 100, drive assembly 130, knife assembly 150, and rotating assembly 170. With reference to FIGS. 1 and 2 in particular, end effector assembly 100 is operably disposed at distal end 92 of shaft 90 and includes a pair of opposing jaw members 110, 120. Each jaw member 110, 120 includes a distal jaw portion 110a, 120a and a proximal flange portion 110b, 120b extending proximally from the respective distal jaw portion 110a, 120a. Distal jaw portions 110a, 120a of jaw members 110, 120, respectively, each include an electrically-insulative outer jaw housing 111, 121 and an electrically-conductive plate 112, 122 disposed atop respective jaw housings 111, 121, although other configurations are also contemplated. Plates 112, 122 of jaw members 110, 120, respectively, are adapted to connect to any suitable source of energy, e.g., electrosurgical, ultrasonic, microwave, light, etc., via first and second lead wires 119, 129 (FIGS. 4A and 4B) for conducting energy therebetween and through tissue grasped between jaw members 110, 120 to treat, e.g., seal, tissue. In one particular configuration, end effector assembly 100 defines a bipolar configuration wherein plate 112 is charged to a first electrical potential and plate 122 is charged to a second, different electrical potential such that an electrical potential gradient is created for conducting energy between plates 112, 122 and through tissue grasped therebetween for treating e.g., sealing, tissue.

With reference to FIG. 2, proximal flange portions 110b, 120b of jaw members 110, 120, respectively, are pivotably coupled to one another about a first pivot pin 102. Proximal flange portions 110b, 120b each further define drive slots 103a, 103b that are angled relative to one another. A second pivot pin 104 is disposed within drive slots 103a, 103b and engaged to drive bar 132 of drive assembly 130. Thus, reciprocation of drive bar 132 through shaft 90 (FIG. 1) and relative to jaw members 110, 120 urges second pivot pin 104 to translate along slots 103a, 103b to thereby pivot jaw members 110, 120 relative to one another between a spaced-apart position and an approximated position. End effector assembly 100 is designed as a unilateral assembly wherein jaw member 110 is operably coupled to drive bar 132 while jaw member 120 is fixedly engaged to shaft 90 (FIG. 1) such that proximal translation of drive bar 132 relative to jaw member 110 pulls jaw member 110 to pivot relative to jaw member 120 towards the approximated position and such that distal translation of drive bar 132 relative to jaw member 110 urges jaw member 110 to pivot relative to jaw member 120 towards the spaced-apart position. Alternatively, end effector assembly 100 may be configured as a bilateral assembly, i.e., wherein both jaw member 110 and jaw member 120 are operably coupled to drive bar 132 and movable relative to shaft 90 (FIG. 1), and/or the configuration of slots 103a, 103b may be reversed such that distal translation of drive bar 132 pivots jaw members 110,120 towards the approximated position while proximal translation of drive bar 132 pivots jaw members 110,120 back towards the spaced-apart position.

Continuing with reference to FIG. 2, one or both of jaw members 110, 120 may further define a knife channel 125 extending longitudinally therethrough. Knife channel(s) 125 is configured to permit reciprocation of a knife 152 of knife assembly 150 therethrough. Knife 152 defines a distal cutting edge (not shown) and is selectively translatable relative to jaw members 110, 120 between a retracted position, wherein knife 152 is positioned proximally of distal jaw portions 110a, 120b of jaw members 110, 120, and an extended position, wherein knife 152, led by the distal cutting edge, extends through knife channel(s) 125 and between distal jaw portions 110a, 120b of jaw members 110, 120 to cut tissue grasped therebetween. Knife 152 is coupled to and extends distally from a knife drive bar 154 of knife assembly 150. Knife drive bar 154 is selectively translatable through shaft 90 (FIG. 1) and relative to jaw members 110, 120 for translating knife 152 between the retracted and extended positions.

Referring to FIGS. 4A and 4B, in conjunction with FIG. 2, drive assembly 130 includes a drive bar 132 that, as mentioned above, is operably coupled to jaw members 110, 120 of end effector assembly 100 at the distal end of drive bar 132 via second pivot pin 104. Drive bar 132 extends proximally from end effector assembly 100, through shaft 90, and into first housing component 22a. Drive assembly 130 includes a mandrel 134 slidably disposed about drive bar 132 at the proximal end of drive bar 132. Mandrel 134 defines an annular slot 135 configured to receive transverse pin 51 of handle assembly 30 upon engagement of first and second portions 12, 14 of forceps 10 with one another such that movable handle 40 may be selectively actuated to translate drive bar 132 relative to shaft 90 and, thus, to pivot jaw members 110, 120 between the spaced-apart and approximated positions, as will be detailed below. A sleeve 133 slidably disposed about drive bar 132 is fixedly engaged to mandrel 134 and extends distally from mandrel 134. Sleeve 133 includes a first collar 136 engaged thereto at the distal end thereof. A second collar 138 is slidably disposed about sleeve 133 and is positioned between mandrel 134 and first collar 136. Second collar 138 is fixed to drive bar 132 via a pin 137 extending through a slot defined within sleeve 133. A biasing member 139 is disposed about sleeve 133 between first and second collars 136, 138, respectively, so as to bias second collar 138 distally, thereby biasing drive bar 132 distally relative to shaft 90. As such, with drive bar 132 biased distally, jaw members 110, 120 are biased towards the spaced-apart position.

Knife assembly 150, as mentioned above, includes knife drive bar 154 having knife 152 coupled to and extending distally therefrom. Knife drive bar 154 extends proximally through shaft 90 and into first housing component 22a. Within first housing component 22a and, more specifically, between intermediate and distal supports 24b, 24c, respectively, thereof, a mandrel 156 is slidably disposed about shaft 90. Mandrel 156 is engaged to knife drive bar 154 towards the proximal end of knife drive bar 154, e.g., via a pin extending through a slot defined within shaft 90. Mandrel 156 defines an annular slot 157 configured to receive protrusions 69 of trigger 62 of trigger assembly 60 upon engagement of first and second portions 12, 14 of forceps 10 with one another such that actuation of trigger 62 may be effected to translate knife 152 between the retracted and extended positions, as will be detailed below.

As shown in FIG. 4B, first housing component 22a further includes a knife lockout member 160 coupled to body 23 of first housing component 22a that is configured to inhibit advancement of knife 152 from the retracted position towards the extended position when first and second portions 12, 14, respectively, of forceps 10 are disengaged from one another. Knife lockout member 160 includes a base 162 that is fixedly engaged to body 23 of first housing component 22a and a resilient cantilever arm 164 that extends from base 162. Resilient cantilever arm 164 defines a finger 166 at the free end thereof. Resilient cantilever arm 164 is biased such that finger 166 is biased into position within annular slot 157 of mandrel 156 of knife assembly 150. As a result of finger 166 being disposed within annular slot 157 in the absence of a suitable force to overcome the bias of resilient cantilever arm 164, mandrel 156 is inhibited from being slid along shaft 90 and, thus, knife 152 is inhibited from being translated relative to shaft 90. Upon engagement of first and second portions 12, 14 of forceps 10 with one another, as will be detailed below, finger 166 is urged out of annular slot 157 to thereby permit selective translation of knife 152 between the retracted and extended positions.

With reference to FIGS. 1, 4A, and 4B and with additional reference to FIG. 1, rotating assembly 170 includes a rotation wheel 172 mounted about shaft 90. Slots 21 formed within housing 20 of forceps 10 on either side thereof provide access to rotation wheel 172. Rotation wheel 172 is rotatable relative to housing 20 about 180 degrees in either direction (due to the stop provided by tongue 99 and band 28a, as detailed above), to thereby rotate transmission assembly 80, e.g., together rotating shaft 90, end effector assembly 100, drive assembly 130, and knife assembly 150, relative to housing 20.

Referring to FIGS. 1-3, 5A and 5B, second portion 14 of forceps 10, as mentioned above, includes second housing component 22b of housing 20, handle assembly 30, and trigger assembly 60, which are coupled to and supported by second housing component 22b. Second housing component 22a includes an engagement member 25b that, as mentioned above, is configured to releasably engage resilient engagement finger 25a of first housing component 22a to releasably engage first and second housing components 22a, 22b to one another at the proximal ends thereof. Second housing component 22b further includes apertures 193 that, as mentioned above, are configured to receive protrusions 192 of first housing component 22a to releasably engage first and second housing components 22a, 22b with one another at their proximal ends. Second housing component 22b also supports activation button 52, second contact plate 27b, and includes a cable 54 coupled thereto. Cable 54 is configured to connect to the source of energy for providing energy to forceps 10 via the wires housed therein. Alternatively, forceps 10 may be configured as a portable, battery-powered instrument having on-board power and energy-generating components, e.g., operably coupled to, disposed within, or forming part of second housing components 22b. A plurality of wires 56 interconnect the wires extending through cable 54 with activation button 52 and second contact plate 27b such that, when first and second portion 12, 14, respectively, of forceps 10 are engaged with one another, energy can be selectively supplied to end effector assembly 100 via activation of activation button 52, as will be detailed below.

Handle assembly 30 of second portion 14 of forceps 10 generally includes a movable handle 40 and a fixed handle 50 integrally formed as part of second housing component 22b. Movable handle 40 includes a lever 42 defining a finger hole 43 and a bifurcated neck 44 extending upwardly from lever 42 and into second housing component 22b. Each bifurcated portion of neck 44 is pivotably coupled to the adjacent section of second housing component 22b by a fixed pivot 45 such that movable handle 40 is pivotable relative to fixed handle 50 between an initial position, wherein movable handle 40 is spaced-apart from fixed handle 50, and a compressed position, wherein movable handle 40 is positioned in close proximity to fixed handle 50. Each bifurcated portion of neck 44 includes an extension 46 extending proximally therefrom. Extensions 46 are pivotably coupled to corresponding linkage members 48 at the first ends of linkage members 48 via a floating pivot 49. The second ends of linkage members 48 are engaged to one another via a transverse pin 51 extending therebetween. Alternatively, each linkage member 48 may include a transverse pin extending therethrough, so as to define a split transverse pin. The ends of transverse pin 51 are received within longitudinally-extending recesses 31 defined within opposing sides of second housing component 22b to confine transverse pin 51 to longitudinal movement within recesses 31. As a result of this configuration, pivoting of movable handle 40 from the initial position to the compressed position urges transverse pin 51 proximally within recesses 31 relative to second housing component 22b. On the other hand, return of movable handle 40 from the compressed position to the initial position pulls transverse pin 51 distally within recesses 31 relative to second housing component 22b.

Trigger assembly 60 includes a trigger 62 having a toggle member 63 and a bifurcated arm 66 extending upwardly from toggle member 63 and into second housing component 22b. Trigger 62 is pivotably coupled to housing 20 via a pivot 65, which extends through an intermediate portion 64 of trigger 62. Arm 66 is bifurcated to define a pair of spaced-apart flanges 67. Each flange 67 includes an inwardly-extending protrusion 69 disposed at the free end thereof. Upon pivoting of trigger 62 about pivot pin 65 and relative to second housing component 22b from an un-actuated position to an actuated position, the free ends of flanges 67 are urged distally. On the other hand, return of trigger 62 from the actuated position back to the un-actuated position urges the free ends of flanges 67 proximally. A biasing member (not shown) may be provided for biasing trigger 62 towards the un-actuated position, although other configurations are also contemplated. As detailed below, upon coupling of trigger assembly 60 with knife assembly 150, trigger 62 is selectively actuatable to deploy knife 152 (FIG. 2).

With reference to FIGS. 1 and 3-5B, the assembly, use, and operation of forceps 10 is detailed. Prior to initial use, or in advance of each subsequent use once any disposable components have been replaced and any reusable components sterilized and/or otherwise prepared for reuse, forceps 10 must be assembled. In order to assemble forceps 10, first and second portions 12, 14 of forceps 10 are engaged to one another. More specifically, as shown in FIG. 3, first and second housing components 22a, 22b are brought into approximation with one another sufficiently so as to allow protrusions 192 (FIG. 6A) of first housing component 22a to snap into engagement with (or otherwise engage) apertures 193 of second housing component 22b to engage first and second housing components 22a, 22b at the distal ends thereof, and such that shoulder 26a of finger 25a of first housing component 22a is engaged with corresponding shoulder 26b of engagement member 25b of second housing component 22b to engage first and second housing components 22a, 22b to one another at the proximal ends thereof.

Concurrently or near-concurrently with the engagement of first and second housing components 22a, 22b at the proximal and distal ends thereof, the approximation of housing components 22a, 22b relative to one another operably couples drive assembly 130 of transmission assembly 80 of first portion 12 with handle assembly 30 of second portion 14, operably couples knife assembly 150 of transmission assembly 80 of first portion 12 with trigger assembly 60 of second portion 14, and electrically couples cable 54 (which is ultimately to be coupled to the source of energy) and activation button 52 of second portion 14 with plates 112, 122 of jaw members 110, 120, of end effector assembly 100 of transmission assembly 80 of first portion 12.

With respect to the operable coupling of drive assembly 130 with handle assembly 30, the approximation of first and second housing components 22a, 22b relative to one another urges mandrel 134 of drive assembly 130 about transverse pin 51 of handle assembly 30 such that transverse pin 51 is received within annular slot 135 of mandrel 134. With transverse pin 51 received within annular slot 135 of mandrel 134, movable handle 40 may be pivoted from the initial position to the compressed position to translate mandrel 134, sleeve 133, and first collar 136 proximally. Proximal translation of first collar 136 urges biasing member proximally into contact with second collar 138 under sufficient urging so as to at least partially compress biasing member 139 and translate second collar 138 proximally. Proximal translation of drive bar 132, in turn, pivots jaw members 110, 120 towards the approximated position. Return of movable handle 40 to the initial position allows drive bar 132 to be returned distally under the bias of biasing member 139 such that jaw members 110, 120 are pivoted back to the spaced-apart position. Put more generally, upon engagement of first and second housing components 22a, 22b, drive assembly 130 is operably coupled with handle assembly 30 such that movable handle 40 of handle assembly 30 may be selectively actuated to approximate jaw members 110, 120 for grasping tissue therebetween and returned, e.g., released, to return jaw members 110, 120 to the spaced-apart position.

With respect to the operable coupling of knife assembly 150 with trigger assembly 60, the approximation of first and second housing components 22a, 22b relative to one another urges mandrel 156 of knife assembly 150 between flanges 67 of trigger 62. Knife lockout member 160, as mentioned above, maintains mandrel 156 in fixed position relative to first housing component 22a, thus helping to ensure that mandrel 156 and flanges 67 are properly aligned with one another during engagement of first and second housing components 22a, 22b. As mandrel 156 is inserted between flanges 67, protrusions 69 of flanges 67 are positioned to at least partially extend into annular slot 157 of mandrel 156. Additionally, upon insertion of mandrel 156 between flanges 67, the free ends of flanges 67 contact finger 166 of resilient cantilever arm 164 of knife lockout member 160 and urge finger 166 out of annular slot 157 of mandrel 156. With protrusions 69 at least partially disposed within annular slot 157 and with finger 166 no longer disposed within annular slot 157, trigger 62 may be pivoted relative to second housing component 22b from the un-actuated position to the actuated position to urge mandrel 156 and, thus, knife drive bar 154 distally, thereby translating knife 152 from the retracted position to the extended position to cut tissue grasped between jaw members 110, 120. That is, upon engagement of first and second housing components 22a, 22b, knife assembly 150 is operably coupled with trigger assembly 60 such that trigger 62 may be selectively actuated to deploy knife 152.

With respect to electrically coupling cable 54 and activation button 52 of second portion 14 with plates 112, 122 of jaw members 110, 120 of end effector assembly 100 of first portion 12, as mentioned above, first housing component 22a includes first contact plate 27a, which is electrically coupled to plates 112, 122 of jaw members 110, 120 via lead wires 119, 129, and second housing component 22b includes second contact plate 27b, which is electrically coupled to activation button 52 and cable 54 via wires 56. Upon approximation of first and second housing components 22a, 22b, first and second contact plates 27a, 27b mate with one another to electrically couple first and second contact plates 27a, 27b with one another. With contact plates 27a, 27b electrically coupled to one another, and once cable 54 is connected to the source of energy, activation button 52 may be selectively activated to supply energy to plates 112, 122 of jaw members 110, 120, respectively, for treating, e.g., sealing, tissue grasped therebetween. First and second contact plates 27a, 27b may each include multiple contacts (not shown) that are electrically isolated from one another such that energy may be independently supplied from the source of energy to plates 112, 122 of jaw members 110, 120, e.g., for bipolar use, although other configurations are also contemplated. Additional contacts of first and second contact plates 27a, 27b may also be provided, e.g., for transmitting control, feedback, and/or other signals between end effector assembly 100 and the source of energy.

Referring generally to FIGS. 1-3, once forceps 10 has been assembled, as detailed above, and cable 54 connected to the source of energy, forceps 10 is ready for use. In use, forceps 10 is initially inserted into the surgical site and end effector assembly 100 is manipulated, e.g., translated and/or rotated, such that tissue to be treated and/or cut is disposed between jaw members 110, 120. Once positioned as desired, movable handle 40 is pivoted from the initial position towards the compressed position to approximate jaw members 110, 120 about tissue and grasp tissue therebetween. As movable handle 40 reaches the compressed position, jaw members 110, 120 impart an appropriate grasping pressure on tissue disposed therebetween, e.g., as a result of the disposition of biasing member 139 between first and second collars 136, 138, respectively. Further, once the compressed position has been reached, projection 53 of movable handle 40 is urged into contact with activation button 52 sufficiently so as to activate activation button 52. Activation of activation button 52, as mentioned above, initiates the supply of energy from the source of energy to plates 112, 122 of jaw members 110, 120. As such, energy is conducted between plates 112, 122 and through tissue grasped therebetween to treat, e.g., seal, tissue.

Once tissue has been treated, or where it is only desired to cut tissue, trigger 62 may be pivoted from the un-actuated position to the actuated position to advance knife 152 from the retracted position to the extended position, wherein knife 152 extends between jaw members 110, 120 to cut tissue grasped therebetween. Upon completion of tissue cutting, knife 152 may be returned to the retracted position, e.g., via releasing or returning trigger 62, and jaw members 110, 120 may be returned to the spaced-apart position, e.g., via releasing or returning movable handle 40, to release the treated and/or divided tissue.

At the completion of the procedure, forceps 10 is withdrawn from the surgical site and is disassembled for replacement and/or reprocessing. More specifically, with reference to FIGS. 1, 3, and 6A, in order to disassemble forceps 10, release buttons 196 on either side of first housing component 22a are squeezed inwardly to disengage protrusions 192 from apertures 193, thereby disengaging first and second housing components 22a, 22b from one another at the distal ends thereof. With the distal ends of first and second housing components 22a, 22b disengaged, first and second housing components 22a, 22b may be moved apart from one another to concurrently or near-concurrently: disengage finger 25a of first housing component 22a from engagement member 25b of second housing component 22b; decouple drive assembly 130 from handle assembly 30; decouple knife assembly 150 from trigger assembly 60; and electrically disconnect cable 54 and activation button 52 from end effector assembly 100.

With first and second portions 12, 14 of forceps 10 fully disengaged from one another, first portion 12 may be discarded and second portion 14 sterilized for reuse. However, it is also contemplated that first portion 12 be reusable and/or that second portion 14 be disposable. In either configuration, the ability to disassemble forceps 10 into first and second portion 12, 14 facilitates the replacement of any disposable components and the sterilization of any reusable components.

In order to prepare forceps 10 for reuse, an unused first portion 12 (in embodiment where first portion 12 is disposable) is engaged with the sterilized second portion 14 (in embodiments where second portion 14 is reusable) similarly as detailed above, and forceps 10 may thereafter be operated similarly as detailed above. With respect to first portion 12 in particular, it is envisioned that various differently configured first portions 12 may be provided, such that a particular first portion 12 may be selected depending upon a particular purpose. For example, it is envisioned that the various first portions 12 include differently sized jaw members, differently shaped jaw members, e.g., curved, linear, etc., transmission assemblies configured to impart different grasping pressures in the approximated position of the jaw members, and/or transmission assemblies configured to establish different minimum gap distances between the jaw members in the approximated position. One or more of the various first portions 12 may further include a transmission assembly incorporating mechanical cutting features, e.g., as detailed above, while another one or more of the various first portions 12 may include effector assemblies having electrical cutting features such as those disclosed in U.S. Pat. No. 8,162,940. Additionally, one or more of the various first portions 12 may further include an effector assembly incorporating monopolar functionality, such as that disclosed in U.S. Patent Application Pub. No. 2014/0005663. Thus, customization of forceps 10 to suit a particular purpose may be readily achieved.

Turning now to FIGS. 7-10, another embodiment of an endoscopic surgical forceps provided in accordance with the present disclosure is shown generally identified by reference numeral 1000. Forceps 1000, similar to forceps 10 (FIG. 1), is configured for selective disassembly to facilitate replacement of any disposable components of forceps 1000 and/or sterilization of any reusable components of forceps 1000. More specifically, forceps 1000 is similar to forceps 10 (FIG. 1) and may include any of the features thereof, except that, with respect to forceps 1000, first portion 1012 (FIG. 9) only includes transmission assembly 1080, while second portion 1014 (FIG. 10) includes handle assembly 1030, trigger assembly 1060, and the entirety of housing 1020. Other differences between forceps 1000 and forceps 10 (FIG. 1) will be detailed below, while similarities between forceps 1000 and forceps 10 (FIG. 1) will only be summarized or omitted entirely for purposes of brevity.

Figure 7:
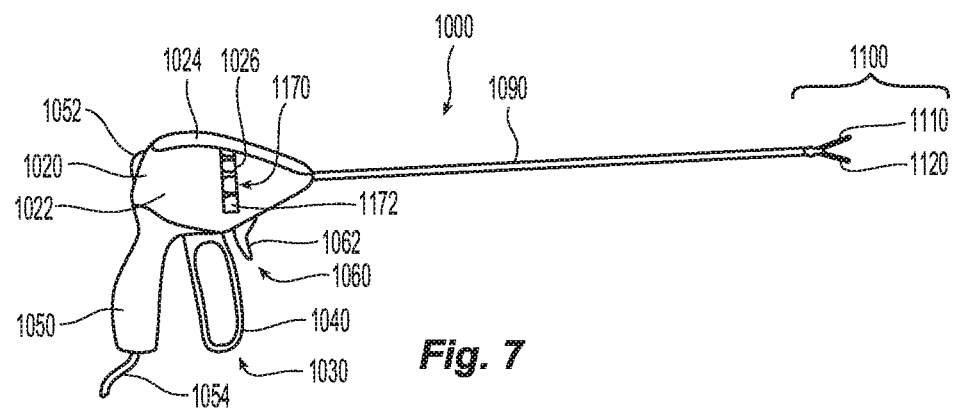
FIG. 7 is a side view of another endoscopic surgical forceps provided in accordance with the present disclosure.
Figure 9:
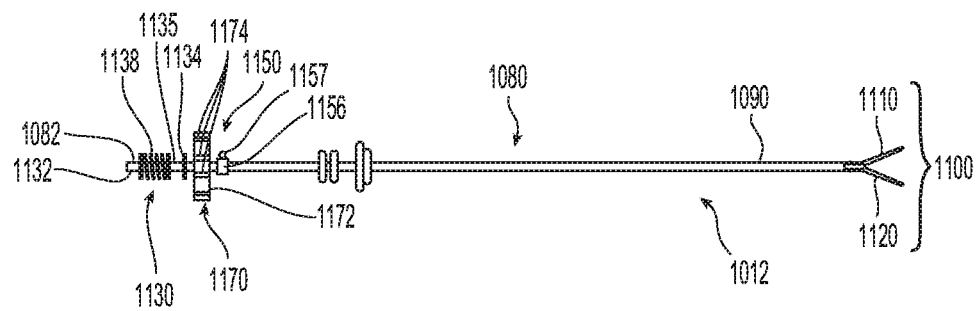
FIG. 9 is a side view of the transmission assembly of the forceps of FIG. 7.
Figure 8:
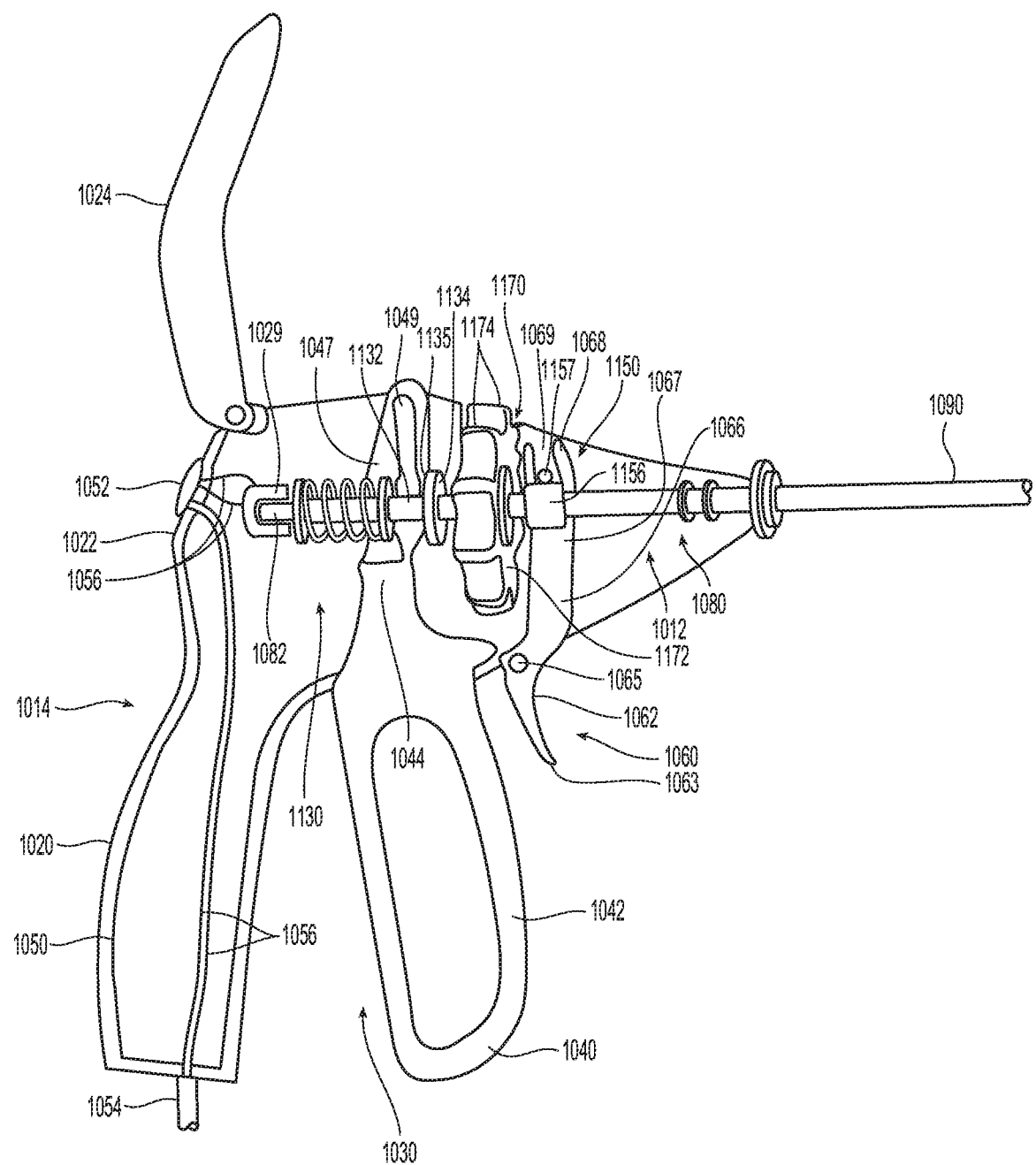
FIG. 8 is a perspective, cut-away view of the proximal end of the forceps of FIG. 7 with the cover of the body assembly disposed in an open position.

Referring to FIGS. 7-9, as mentioned above, transmission assembly 1080 forms first portion 1012 (FIG. 9) of forceps 10. Transmission assembly 1080 includes a shaft 1090, an end effector assembly 1100 disposed at the distal end of shaft 1090, a drive assembly 1130, a knife assembly 1150, and a rotating assembly 1170. Shaft 1090 includes a mandrel 1091 secured thereabout that is configured for rotatable receipt within the distal-most support member of housing 1020 for retaining shaft 1090 in position relative to housing 1020 upon insertion therein. Drive assembly 1130 includes a drive bar 1132 slidably disposed within shaft 1090. Drive bar 1132 is operably coupled to jaw members 1110, 1120 of end effector assembly 1100 at the distal end of drive bar 132 and a mandrel 1134 is coupled to drive bar 1132 towards a proximal end of drive bar 1132 such that translation of mandrel 1134 reciprocates the drive bar 1132 through shaft 1090 to effect pivoting of jaw members 1110, 1120 of end effector assembly 1100 between spaced-apart and approximated positions, similarly as detailed above with respect to forceps 10 (FIG. 1). A biasing member 1138 may be provided for biasing drive bar 1132 distally, thereby biasing jaw members 1110, 1120 towards the spaced-apart position.

Knife assembly 1150 includes a knife drive bar (not shown, similar to knife drive bar 154 of forceps 10 (FIG. 2)) slidably disposed within shaft 1090. The knife drive bar is operably coupled to a knife (not shown, similar to knife 152 of forceps 10 (FIG. 2)) at the distal end of the knife drive bar, and a collar 1156 is coupled to the knife drive bar towards a proximal end of the knife drive bar such that translation of collar 1156 reciprocates the knife drive bar through shaft 1090 to effect extension and retraction of the knife relative to jaw members 1110, 1120, similarly as detailed above with respect to forceps 10 (FIG. 1). Collar 1156 further includes a transverse pin 1157 mounted thereon for operably coupling knife assembly 1150 to trigger assembly 1060, as detailed below. Rotating assembly 1170 includes a rotation wheel 1172 that is rotatable in either direction to rotate end effector assembly 1100 relative to housing 1020 when transmission assembly 1080 is engaged thereto. Rotation wheel 1172 includes a plurality of radially-extending flanges 1174 to facilitate rotation of rotation wheel 1172 relative to housing 1020.

Figure 10:
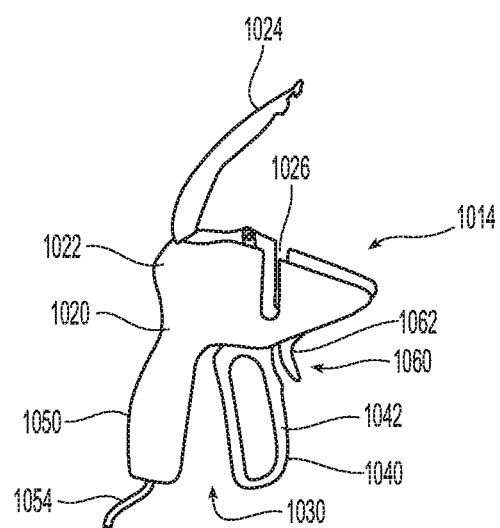
FIG. 10 is a perspective view of the body assembly of the forceps of FIG. 7.

With reference to FIGS. 7, 8, and 10, second portion 1014 of forceps 1000 includes housing 1020, handle assembly 1030, and trigger assembly 1060. Housing 1020 defines a body 1022 having a fixed handle 1050 extending therefrom, and a cover 1024 pivotably coupled to body 1022. Cover 1024 is pivotable relative to body 1022 from a closed position (FIG. 7), wherein cover 1024 and body 1022 cooperate to fully enclose the interior of housing 1020, and an open position (FIG. 8), wherein cover 1024 is displaced relative to body 1022 to provide access to the interior of body 1022, thus facilitating insertion and removal of transmission assembly 1080 from the interior of body 1022. Cover 1024 and body 1022 may further include any suitable releasable engagement features, e.g., snap-fit components, lock rings, etc., for releasably engaging cover 1024 and body 1022 with one another opposite the pivotable end of cover 1024 to releasably secure cover 1024 in the closed position (FIG. 7).

Housing 1020 of second portion 1014 of forceps 1000 further includes a pair of opposed slots 1026 defined therethrough and a plurality of support members (not shown) disposed therein. Slots 1026 provide access to rotation wheel 1172 to permit rotation of end effector assembly 1100 relative to housing 1020 when transmission assembly 1080 is disposed within housing 1020. The support members are configured to rotatably support transmission assembly 1080 within housing 1020 when transmission assembly 1080 is positioned therein.

Continuing with reference to FIGS. 7, 8, and 10, housing 1020 includes an activation button 1052 operably disposed thereon and a cable 1054 extending therefrom. Cable 1054 is configured to connect forceps 1000 to a source of energy (not shown), e.g., a generator, for providing energy to forceps 1000, although forceps 1000 may alternatively be configured as a portable, battery-powered instrument. A plurality of wires 1056 interconnect the wires extending through cable 1054 with activation button 1052. Activation button 1052 is selectively activatable to initiate the supply of energy to end effector assembly 1100 when transmission assembly 1080 is disposed within housing 1020. More specifically, wires 1056 may be electrically coupled to an electrical connection member 1029 of housing 1020. Electrical connection member 1029 includes one or more contacts that are configured to electrically couple to corresponding contacts disposed on an electrical connection member 1082 of transmission assembly 1080. Electrical connection members 1029, 1082 may be electrically coupled to one another in any suitable fashion, e.g., via mating surfaces, male-female engagement, etc., upon insertion of transmission assembly 1080 into housing 1020. Lead wires (not shown, similar to lead wires 119, 129 (FIG. 4B)) extend from electrical connection member 1082, through drive bar 1132 and/or shaft 1090, to jaw members 1110, 1120 of end effector assembly 1100 to permit energy to be supplied thereto for treating, e.g., sealing tissue, similarly as detailed above with respect to forceps 10 (FIG. 1). Other suitable electrical connection configurations are also contemplated.

Handle assembly 1030 of second portion 1014 generally includes a movable handle 1040 and fixed handle 1050, which is integrally formed with housing 1020. Movable handle 1040 includes a lever 1042 and a bifurcated neck 1044 extending upwardly from lever 1042 and into housing 1020. Each bifurcated portion of neck 1044 includes a flange 1047. Each flange 1047 is pivotably coupled to the adjacent side of housing 1020 at the free end of the flange 1047 such that movable handle 1040 is pivotable relative to fixed handle 1050 between an initial position, wherein movable handle 1040 is spaced-apart from fixed handle 1050, and a compressed position, wherein movable handle 1040 is positioned in close proximity to fixed handle 1050. Flanges 1047 each further define elongated tracks 1049 extending therealong and inwardly therefrom. Upon insertion of transmission assembly 1080 into housing 1020, tracks 1049 are received at least partially within an annular slot 1135 of mandrel 1134 of drive assembly 1130, on either side of mandrel 1134, to operably couple handle assembly 1030 with drive assembly 1130. With handle assembly 1030 and drive assembly 1130 operably coupled to one another in this manner, movable handle 1040 may be actuated from the initial position to the compressed position to urge mandrel 1134 and, thus, drive bar 1132, proximally, thereby pivoting jaw members 1110, 1120 relative to one another from the spaced-apart position to the approximated position. Upon release of movable handle 1040, biasing member 1138 serves to return mandrel 1134 distally, thereby returning jaw members 1110, 1120 towards the spaced-apart position.

Trigger assembly 1060 of second portion 1014 generally includes a includes a trigger 1062 having a toggle member 1063 and a bifurcated arm 1066 extending from toggle member 1063 into housing 1020. Trigger 1062 is pivotably coupled to housing 1020 via a pivot 1065. Bifurcated arm 1066 defines a pair of flanges 1067 extending upwardly from pivot 1065. Flanges 1067 of bifurcated arm 1066 each define a u-shaped configuration having a pair of up-rights 1068 defining a longitudinal slot 1069 configured to receive transverse pin 1157 of knife assembly 1150 to operably couple knife assembly 1150 with trigger assembly 1060 upon insertion of transmission assembly 1080 into housing 1020.

Referring again to FIGS. 7-10, the assembly, use, and operation of forceps 1000 is detailed. As the assembly, use, and operation of forceps 1000 is similar to that of forceps 10 (FIG. 1), detailed above, only the differences will be detailed below, while similarities will be summarized or omitted entirely. In order to assemble forceps 1000, cover 1024 of housing 1020 of second portion 1014 is first pivoted from the closed position to the open position (see FIG. 10). With cover 1024 disposed in the open position, first portion 1012, e.g., transmission assembly 1080, may be inserted into second portion 1014, e.g., housing 1020, such that rotation wheel 1172 of rotating assembly 1170 is positioned within slots 1026 and such that shaft 1090 is supported within the support members of housing 1020. Concurrently or near-concurrently with the insertion of transmission assembly 1080 into housing 1020, drive assembly 1130 is operably coupled with handle assembly 1030, knife assembly 1150 is operably coupled with trigger assembly 1060, and cable 1054 (which is ultimately to be coupled to the source of energy) and activation button 1052 are electrically coupled with end effector assembly 1100.

With respect to the operable coupling of drive assembly 1130 with handle assembly 1030, as transmission assembly 1080 is inserted into housing 1020, flanges 1047 of movable handle 1040 are positioned about mandrel 1134 with tracks 1049 disposed within annular slot 1135. As such, movable handle 1040 may be pivoted between the initial and compressed positions to thereby translate mandrel 1134 and, thus, reciprocate drive bar 1132 of drive assembly 1130 through shaft 1090 and relative to end effector assembly 1100 to pivot jaw members 1110, 1120 between the spaced-apart and approximated positions.

With respect to the operable coupling of knife assembly 1150 with trigger assembly 1060, as transmission assembly 1080 is inserted into housing 1020, transverse pin 1157 of knife assembly 1150 is inserted into slots 1069 of flanges 1067 of trigger 1062 such that trigger 1062 may be pivoted from the un-actuated position to the actuated position to translate collar 1156 and, thus, the knife drive bar through and relative to shaft 1090, thereby translating the knife between the retracted and extended positions.

With respect to the electrical coupling of cable 1054 and activation button 1052 with jaw members 1110, 1120 of end effector assembly 1100, as transmission assembly 1080 is inserted into housing 1020, the contacts of electrical connection member 1082 of transmission assembly 1080 engage, mate, or otherwise couple to the corresponding contacts of electrical connection member 1029 to electrically couple wires 1056 with the lead wires extending to jaw members 1110, 1120. Accordingly, once cable 1054 is connected to the source of energy, activation button 1052 may be selectively activated to supply energy to jaw members 1110, 1120 for treating, e.g., sealing, tissue grasped therebetween.

With transmission assembly 1080 inserted into housing 1020 and operably coupled thereto, as detailed above, cover 1024 of housing 1020 may be returned to the closed position to enclose and retain transmission assembly 1080 therein. Thereafter (or prior thereto), cable 1054 is connected to the source of energy. Once this has been achieved, forceps 1000 is ready for use and may be used for grasping, treating, e.g., sealing, and/or cutting tissue, similarly as detailed above with respect to forceps 10 (FIG. 1). Disassembly of forceps 1000 after use is effected in the opposite manner as the assembly detailed above.

Turning to FIGS. 11A-13, a tool provided in accordance with the present disclosure and configured to facilitate the insertion and/or removal of transmission assembly 1080 to/from housing 1020 is shown generally identified by reference numeral 500. In particular, as will become apparent in view of the following, tool 500 is configured to help ensure: that jaw members 1110, 1120 are maintained in the appropriate position, e.g., the closed position (although tool may alternatively be configured to maintain jaw members 1110, 1120 in the open position), during coupling of transmission assembly 1080 with drive assembly 1030; that knife assembly 1150 is disposed in the proper orientation for coupling with trigger assembly 1060; that rotation wheel 1172 of rotation assembly 1170 is properly aligned relative to slots 1026 of housing 1020; and that electrical connection member 1082 is properly aligned for coupling with electrical connection member 1029. Tool 500 may further include a barcode, RFID chip, or other identification component (not shown) suitable for enabling an energy source such as a generator to recognize tool 500 and, thus, the transmission assembly 1080 associated therewith. Alternatively or additionally, the transmission assembly 1080 (and/or any of the other first portions detailed herein) may similarly include an identification component (not shown) for similar purposes.

Tool 500 generally includes a base 510, a handle 520, first, second, and third support members 530, 540, 550, respectively, and an actuation assembly 560. Tool 500 may be formed via a one-shoe injection molding process with the exception of actuation assembly 560, which is then coupled to the one-shot component. Other suitable manufacturing methods are also contemplated. Tool 500 may be configured as a sterilizable component for repeated use or may be configured as a limited-use, disposable component, e.g., a single-use component or a single-procedure component that allows engagement/disengagement of multiple transmission assemblies 1080 during the course of a single procedure.

Base 510 of tool 500 support handle 520 and actuation assembly 560 and includes support members 530, 540, 550 disposed at a first end, intermediate portion, and second end, respectively, thereof. Handle 520 defines a first finger hole 522 and a second finger hole 524. Finger holes 522, 524 are configured to facilitate grasping and manipulating tool 500, e.g., to facilitate the insertion and removal of transmission assembly 1080 to/from housing 1020.

First, second, and third support members 530, 540, 550 are configured to releasably engage transmission assembly 1080. More specifically, first support member 530, disposed at the proximal end of tool 500, includes a pair of spring fingers 532 interconnected via a living hinge 533 and cooperating to define an annular recess 534 therebetween. Spring fingers 532 define tapered free ends 536 such that, upon urging of first support member 530 about drive bar 1132, free ends 536 of spring fingers 532 are urged apart from one another to enlarge the spacing between free ends 536 of spring fingers 532 to permit passage of drive bar 1132 into annular recess 534. Once drive bar 1132 is received within annular recess 534, spring fingers 532 are permitted to return under bias to their at-rest position, wherein the spacing therebetween is less than a diameter of drive bar 1132 such that drive bar 1132 is retained within annular recess 534.

Second support member 540, disposed at the distal end of tool 500, is similar to first support member 530 and includes a pair of tapered spring fingers 542 interconnected via a living hinge 543 and cooperating to define an annular recess 544 therebetween. Second support member 540 is configured to receive and releasably retain shaft 1090 within annular recess 544 thereof in similar fashion as detailed above with respect to the releasable engagement of drive bar 1132 within annular recess 534 of first support member 530.

Third support member 550 is interdisposed between first and second support members 530, 540 and defines a living hinge 552 having a V-shaped cutout 554. Living hinge 552 is configured to frictionally receive and retain one of the flanges 1174 of rotation wheel 1172 within V-shaped cutout 554 to maintain a fixed rotational orientation of transmission assembly 1080 relative to tool 500 when engaged thereto.

Figure 12A:
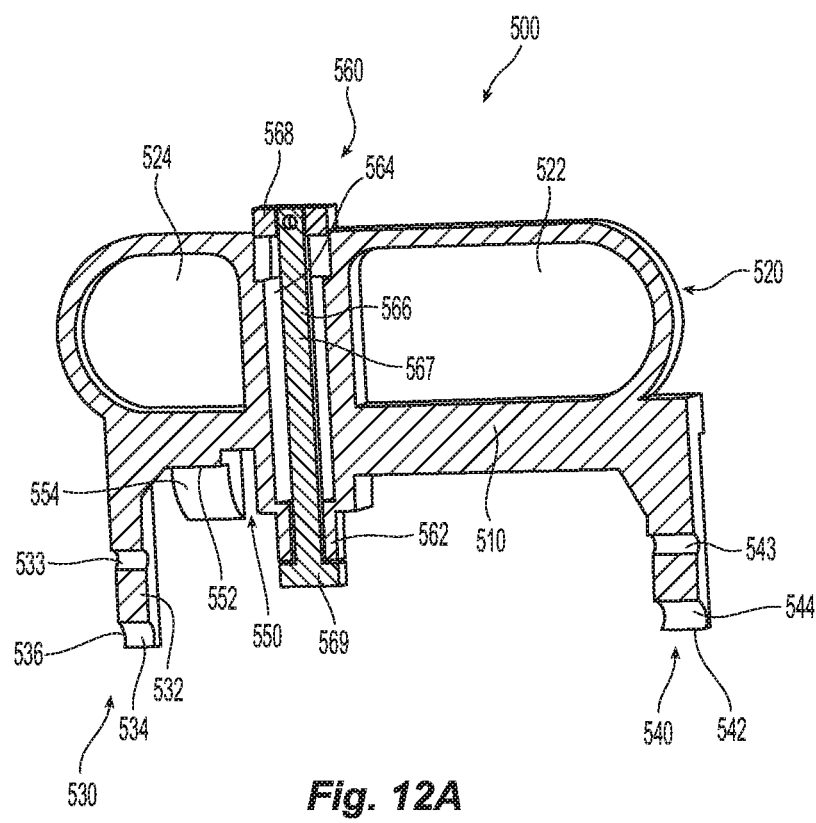
FIG. 12A is a longitudinal, cross-sectional view of the tool of FIG. 11A, disposed in a grasping condition.
Figure 12B:
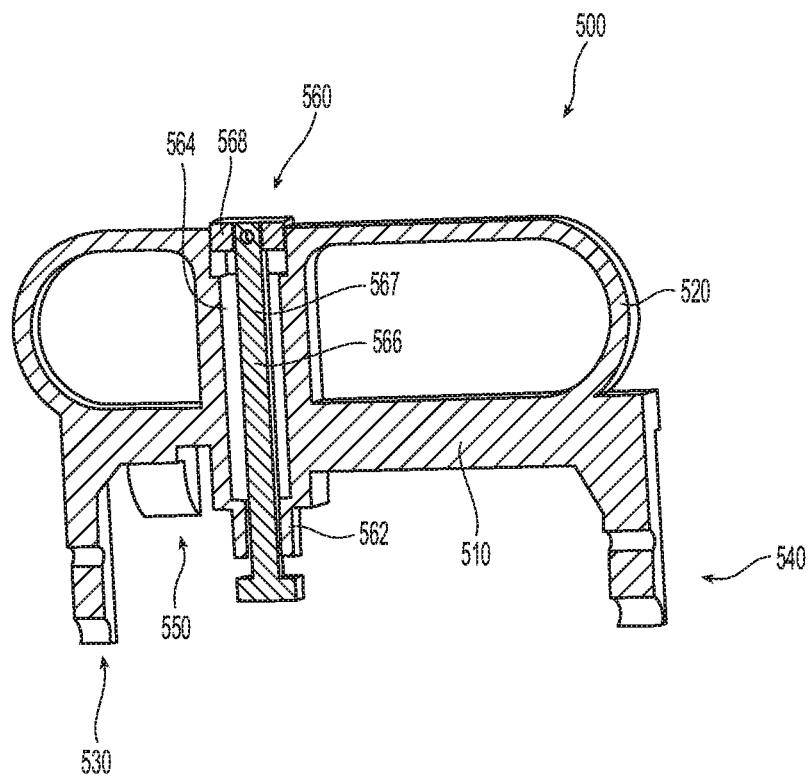
FIG. 12B is a longitudinal, cross-sectional view of the tool of FIG. 11A, disposed in an ejecting position.

With reference to FIGS. 12A and 12B, actuation assembly 560 includes an outer shaft 562 defining a lumen 564 and a plunger 566 slidably disposed within lumen 564. Plunger 566 includes a body portion 567, an actuator 568 disposed one end of the body portion 567, and a foot 569 disposed at the opposite end of the body portion 567. Actuator 568 is selectively depressible from an initial position, wherein foot 569 is positioned adjacent outer shaft 562, and an actuated position, wherein body portion 567 is advanced through lumen 564 of outer shaft 562 such that foot 569 extends in spaced-apart relation from outer shaft 562. As will be detailed below, in the actuated position of actuator 568, foot 569 extends sufficiently from outer shaft 562 so as to contact transmission assembly 1080 and urge transmission assembly 1080 apart from tool 500 such that transmission assembly 1080 is disengaged from first, second, and third supports 530, 540, 550, respectively.

Figure 11A:
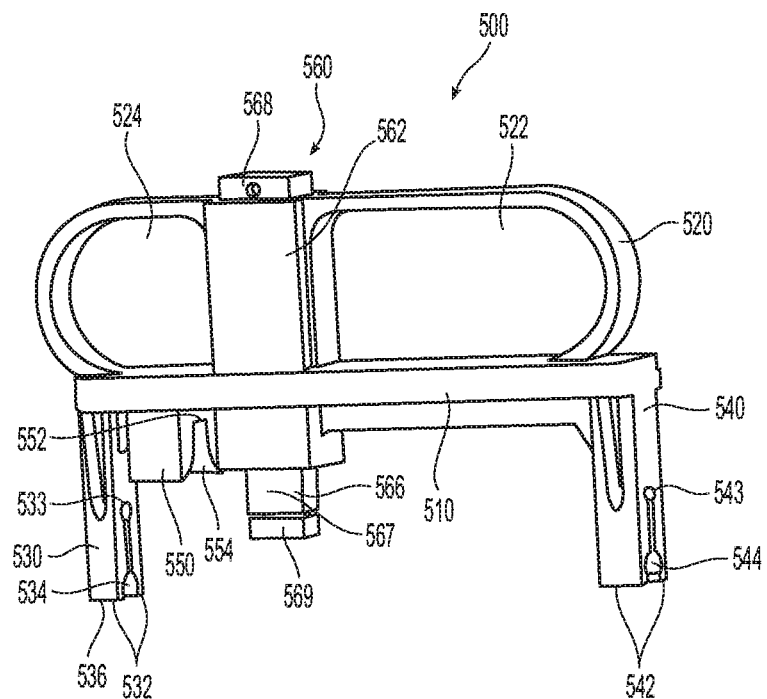
FIG. 11A is a perspective view of a tool provided in accordance with the present disclosure and configured for use in inserting/removing the transmission assembly of FIG. 9 into/from the body assembly of FIG. 10.
Figure 11B:
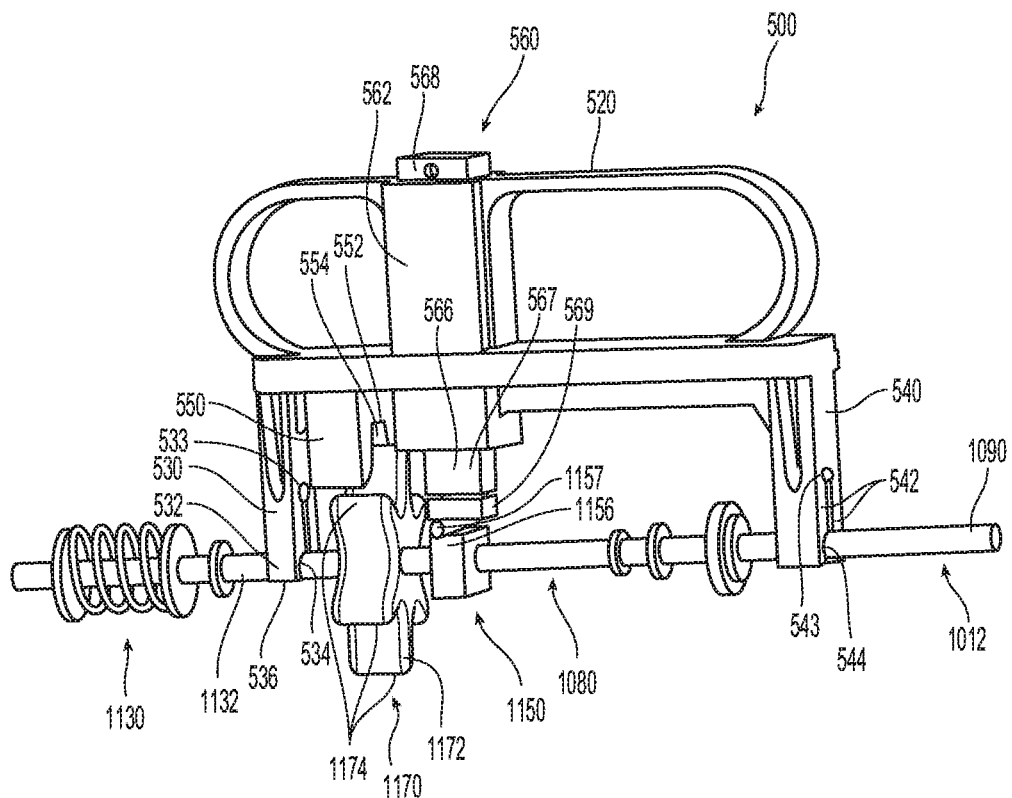
FIG. 11B is a perspective view of the tool of FIG. 11A including the transmission assembly of FIG. 9 coupled thereto.
Figure 13:
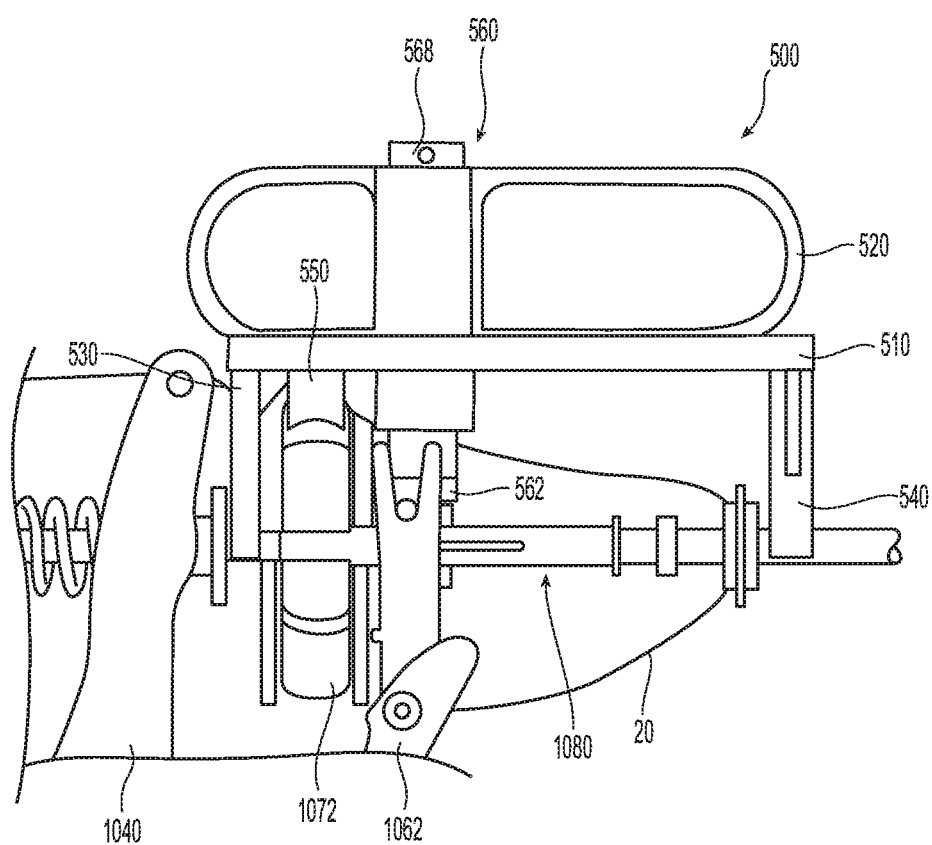
FIG. 13 is a side, cut-away view of the forceps of FIG. 7 and the tool of FIG. 11A with the tool being utilized to insert the transmission assembly of FIG. 9 into the body assembly of FIG. 10.
Figure 14:
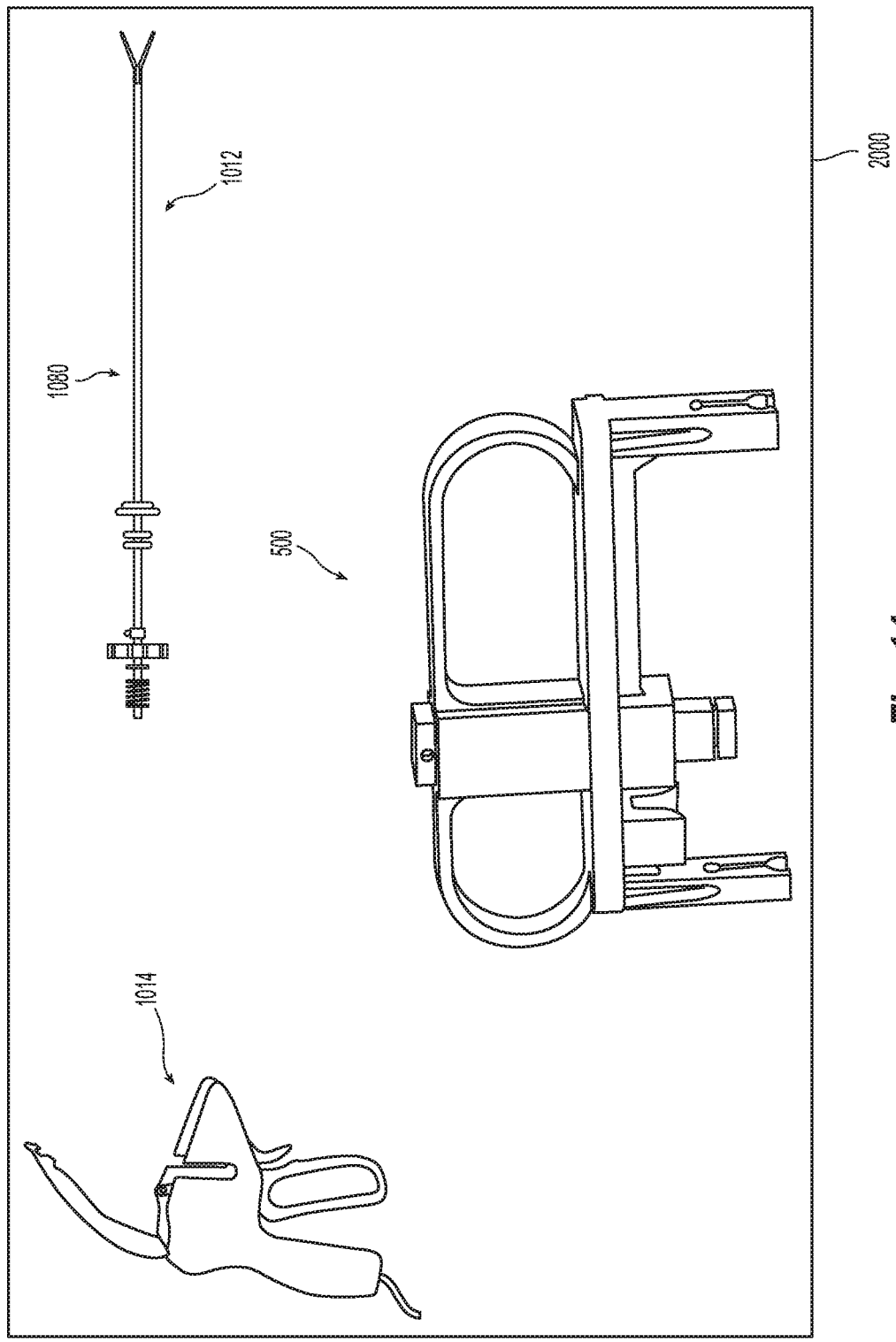
FIG. 14 illustrates a system provided in accordance with the present disclosure incorporating first and second portions of a forceps and a tool utilized for assembling the forceps.

Referring to FIG. 13, in conjunction with FIGS. 11A-11B the use and operation of tool 500 for inserting transmission assembly 1080 into and operably engaging transmission assembly 1080 within housing 1020 is described. Initially, tool 500 is engaged about transmission assembly 1080. Tool 500 may be engaged about transmission assembly 1080 during manufacturing and sold in this manner, or may be provided separate from transmission assembly 1080 but sold together. For example, with additional reference to FIG. 14, a kit 2000 may be provided including tool 500, transmission assembly 1080 (and/or a plurality of different (or similar) transmission assemblies), and one or more housings 1020. Alternatively, tool 500 may be sold separately and only housing(s) 1020 and transmission assembly(s) 1080 are provided in the kit 2000.

Engaging tool 500 about transmissions assembly 1080 is accomplished by urging tool 500 into contact with transmission assembly 1080 under sufficient force such that first support member 530 receives drive bar 1132 within annular recess 534 thereof, second support member 540 receives shaft 1090 within annular recess 544 thereof, and third support member 550 receives one of the flanges 1174 of rotation wheel 1172 within V-shaped cutout 554 thereof. At this point, actuator 568 is disposed in the initial position, wherein foot 569 is disposed in close proximity to outer shaft 562, spaced-apart from transmission assembly 1080.

With transmission assembly 1080 engaged with tool 500, as detailed above, handle 520 of tool 500 may be grasped, e.g., using finger hole 522 and/or finger hole 524, and maneuvered to insert transmission assembly 1080 into housing 1020. More specifically, with cover 1024 of housing 1020 disposed in the open position, tool 500 is maneuvered to insert transmission assembly 1080 into housing 1020 such that rotation wheel 1172 of rotating assembly 1170 is positioned within slots 1026 (FIG. 10), shaft 1090 is supported via the support members, electrical connection member 1082 is electrically coupled with electrical connection member 1029, drive assembly 1130 is operably coupled with handle assembly 1030, and knife assembly 1150 is operably coupled with trigger assembly 1060.

Once transmission assembly 1080 has been properly engaged within second portion 1014 of forceps 1000, tool 500 may be disengaged from transmission assembly 1080 and cover 1024 returned to the closed position to complete the assembly of forceps 1000 and ready forceps 1000 for use. In order to disengage tool 500 from transmission assembly 1080, actuator 568 is depressed to the actuated position to urge foot 569 to extend from outer shaft 562 and into contact with transmission assembly 1080 sufficiently so as to urge transmission assembly 1080 apart from tool 500 and under sufficient force such that transmission assembly 1080 is disengaged from first, second, and third supports 530, 540, 550, respectively. Thereafter, tool 500 may be removed and cover 1024 moved to the closed position to ready forceps 1000 for use.

The removal of transmission assembly 1080 from housing 1020 after use is effected by opening cover 1024; urging tool 500 into contact with transmission assembly 1080 under sufficient force such that first support member 530 receives drive bar 1132 within annular recess 534 thereof, second support member 540 receives shaft 1090 within annular recess 544 thereof, and third support member 550 receives one of the flanges 1174 of rotation wheel 1172 within V-shaped cutout 554 thereof; and withdrawing transmission assembly 1080 from housing 1020, using tool 500, to disengage transmission assembly 1080 from handle assembly 1030 and trigger assembly 1060. Once removed from housing 1020, actuator 568 may be actuated to release tool 500 from transmission assembly 1080, similarly as detailed above.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

In particular, the transmission assemblies of the present disclosure may be configured for use with such robotic systems in addition to being used with manually-operated assemblies. That is, depending on the particular procedure, the transmission assembly may be coupled to a manually-operated assembly or a robotic system. Thus, the transmission assemblies of the present disclosure are capable of being used in either configuration without the need for multiple transmission assemblies depending on whether robotic or manual surgery is desired.

With respect to coupling the transmission assembly to a robotic system, the robotic system would include suitable components, such as those detailed above, capable of manipulating and actuating the transmission assembly. The robotic surgical systems may further be employed with one or more consoles that are next to the operating theater or located in a remote location. In this instance, one team of surgeons or nurses may prep the patient for surgery and configure the robotic surgical system with one or more of the transmission assemblies while another surgeon (or group of surgeons) remotely control the transmission assembly(s) via the robotic surgical system. As can be appreciated, a highly skilled surgeon may perform multiple operations in multiple locations without leaving his/her remote console which can be both economically advantageous and a benefit to the patient or a series of patients.

In use, the robotic arms of the surgical system are typically coupled to a pair of master handles by a controller. The handles can be moved by the surgeon to produce a corresponding movement, manipulation, and/or actuation of the transmission assembly(s) coupled thereto. The movement of the master handles may be scaled so that the operably components of the transmission assembly(s) has a corresponding movement that is different, smaller or larger, than the movement performed by the operating hands of the surgeon. The scale factor or gearing ratio may be user-adjustable so that the operator can control the resolution of the operable components of the transmission assembly(s).

The master handles of the robotic system may further include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   a first portion defining an upper housing component, the upper housing component defining a proximal end portion thereof, the first portion including:
   a shaft;
   an end effector assembly disposed at a distal end of the shaft, the end effector assembly including first and second jaw members movable relative to one another between a spaced-apart position and an approximated position;
   a drive assembly including a drive bar slidably disposed within the shaft and coupled to the end effector assembly at a distal end of the drive bar such that translation of the drive bar relative to the shaft moves the first and second jaw members between the spaced-apart and approximated positions; and
   a first contact plate, the first contact plate defining a bottom surface;
   a second portion defining a lower housing component, the lower housing component defining a proximal end portion thereof, a longitudinally-extending recess formed in the proximal end portion of the lower housing component, the second portion including:
   a handle assembly including a movable handle, the movable handle coupled to the lower housing component and movable relative thereto between a first position and a second position, the handle assembly including an extension member extending from the movable handle, a linkage member, a floating pivot pivotably coupling the extension member with the linkage member, and a transverse pin arranged in the linkage member, wherein the transverse pin is arranged in the longitudinally-extending recess formed in the proximal end portion of the lower housing component, the longitudinally-extending recess configured to allow longitudinal translation of the transverse pin therein; and
   a second contact plate, the second contact plate defining an upper surface,
   wherein the upper housing component and the lower housing component are releasably couplable with one another and wherein coupling of the upper housing component and the lower housing component with one another operably couples the linkage member of the movable handle with the drive bar such that moving the movable handle between the first and second positions moves the jaw members between the spaced-apart and approximated positions, and
   wherein the proximal end portion of the upper housing component is releasably couplable with the proximal end portion of the lower housing component, and when the upper housing component and the lower housing component are releasably couplable with one another, the bottom surface of the first contact plate is in contact with the upper surface of the second contact plate to electrically connect the upper housing component with the lower housing component, wherein the drive assembly further includes a mandrel coupled to the drive bar, the mandrel defining a slot, and wherein, upon coupling of the first and second portions with one another, the transverse pin of the handle assembly is received within the slot of the mandrel such that moving the movable handle between the first and second positions moves the jaw members between the spaced-apart and approximated positions.

2. The forceps according to claim 1, wherein the drive assembly further includes a mandrel coupled to the drive bar, the mandrel defining a slot, wherein the movable handle includes at least one track disposed thereon, and wherein, upon coupling of the upper housing component and the lower housing component with one another, at least a portion of the at least one track is received within the slot of the mandrel such that moving the movable handle between the first and second positions moves the jaw members between the spaced-apart and approximated positions.

3. The forceps according to claim 1, wherein the first portion further includes a first electrical connector electrically coupled to at least one of the first and second jaw members, wherein the second portion further includes a second electrical connector adapted to connect to a source of energy, and wherein, upon coupling of the upper housing component and the lower housing component with one another to bring the bottom surface of the first contact plate into contact with the upper surface of the second contact plate, the first and second electrical connectors are electrically coupled with one another to enable energy to be supplied from the energy source to the at least one of the first and second jaw members.

4. The forceps according to claim 1, wherein the first portion further includes a knife assembly, the knife assembly including a knife drive bar slidably disposed within the shaft and a knife extending distally from the knife drive bar, the knife assembly configured such that translation of the knife drive bar relative to the shaft moves the knife relative to the end effector assembly between a retracted position and an extended position, wherein the knife extends between the first and second jaw members, wherein the second portion further includes a trigger assembly including a trigger, the trigger coupled to the at least a portion of the lower housing component and movable relative thereto between an un-actuated position and an actuated position, and wherein, coupling of the upper housing component and the lower housing component with one another operably couples the trigger with the knife drive bar such that moving the trigger between the un-actuated and actuated positions moves the knife between the retracted and extended positions.

5. The forceps according to claim 4, wherein the knife assembly further includes a mandrel coupled to the knife drive bar, the mandrel defining a slot, wherein the trigger includes at least one protrusion disposed thereon, and wherein, upon coupling of the upper housing component and the lower housing component with one another, at least a portion of the at least one protrusion is received within the slot of the mandrel such that moving the trigger between the un-actuated and actuated positions moves the knife between the retracted and extended positions.

6. The forceps according to claim 4, wherein the knife assembly further includes a collar coupled to the knife drive bar, the collar including a transverse pin engaged thereto, wherein the trigger defines at least one slot, and wherein, upon coupling of the upper housing component and the lower housing component with one another, the transverse pin of the knife assembly is received within the at least one slot of the trigger such that moving the trigger between the un-actuated and actuated positions moves the knife between the retracted and extended positions.

7. The forceps according to claim 4, wherein the first portion further includes a knife lockout member, the knife lockout member movable between a locked position, wherein the knife lockout member is coupled to the knife drive bar to inhibit translation of the knife drive bar relative to the shaft, and an unlocked position, wherein the knife lockout member is decoupled from the knife drive bar to permit translation of the knife drive bar relative to the shaft, wherein the knife lockout member is moved from the locked position to the unlocked position upon coupling of the first and second portions with one another.

8. The forceps according to claim 1, wherein the first portion further includes a rotation assembly having a rotation wheel coupled to the shaft and the drive assembly, and wherein, with the upper housing component and the lower housing component coupled with one another, the rotation wheel is rotatable relative to the second portion to rotate the end effector assembly relative to the second portion.

* * * * *